US010628834B1

(12) United States Patent
Agarwal et al.

(10) Patent No.: US 10,628,834 B1
(45) Date of Patent: Apr. 21, 2020

(54) FRAUD LEAD DETECTION SYSTEM FOR EFFICIENTLY PROCESSING DATABASE-STORED DATA AND AUTOMATICALLY GENERATING NATURAL LANGUAGE EXPLANATORY INFORMATION OF SYSTEM RESULTS FOR DISPLAY IN INTERACTIVE USER INTERFACES

(71) Applicant: Palantir Technologies Inc., Palo Alto, CA (US)

(72) Inventors: Rahul Agarwal, Palo Alto, CA (US); Diane Wu, Palo Alto, CA (US)

(73) Assignee: Palantir Technologies Inc., Palo Alto, CA (US)

( * ) Notice: Subject to any disclaimer, the term of this patent is extended or adjusted under 35 U.S.C. 154(b) by 49 days.

(21) Appl. No.: 15/181,712

(22) Filed: Jun. 14, 2016

Related U.S. Application Data

(60) Provisional application No. 62/180,495, filed on Jun. 16, 2015, provisional application No. 62/211,327, filed on Aug. 28, 2015.

(51) Int. Cl.
*G16H 10/60* (2018.01)
*G06Q 30/00* (2012.01)
(Continued)

(52) U.S. Cl.
CPC ......... *G06Q 30/0185* (2013.01); *G06N 20/00* (2019.01); *G16H 10/60* (2018.01); *G06Q 50/24* (2013.01)

(58) Field of Classification Search
CPC ......... G06Q 50/22; G06Q 50/24; G06Q 40/08
See application file for complete search history.

(56) References Cited

U.S. PATENT DOCUMENTS 5,241,625 A 8/1993 Epard et al.
5,670,987 A 9/1997 Doi et al.
(Continued)

FOREIGN PATENT DOCUMENTS

CN 102546446 7/2012
CN 103167093 6/2013
(Continued)

OTHER PUBLICATIONS

Amnet, "5 Great Tools for Visualizing Your Twitter Followers," posted Aug. 4, 2010, http://www.amnetblog.com/component/content/article/115-5-grate-tools-for-visualizing-your-twitter-followers.html.
(Continued)

*Primary Examiner* — Lena Najarian
(74) *Attorney, Agent, or Firm* — Knobbe Martens Olson & Bear LLP

(57) ABSTRACT

Systems and methods are described for automatically processing data stored in one or more databases using machine learning to detect entities (such as health care providers, health care plan members, patients, pharmacies, and so forth) associated with health care claims that are suspected of fraudulent, wasteful, and/or abusive activity. The techniques may further or alternatively involve generating and presenting, for a set of suspected entities, natural language explanatory information explaining how and/or why each of the respective suspected entities is considered to be suspected of fraudulent, wasteful, and/or abusive activity. Feedback provided by fraud analysts and/or other subject matter experts in the misuse detection space is used to facilitate misuse detection and misuse detection presentation.

17 Claims, 9 Drawing Sheets

(51) Int. Cl.
  *G06N 20/00* (2019.01)
  *G06Q 50/24* (2012.01)

(56) References Cited

U.S. PATENT DOCUMENTS

| | | |
|---|---|---|
| 5,819,226 A | 10/1998 | Gopinathan et al. |
| 5,826,021 A | 10/1998 | Mastors et al. |
| 5,832,218 A | 11/1998 | Gibbs et al. |
| 5,845,300 A | 12/1998 | Comer |
| 5,878,434 A | 3/1999 | Draper et al. |
| 5,892,900 A | 4/1999 | Ginter et al. |
| 5,893,072 A | 4/1999 | Zizzamia |
| 5,897,636 A | 4/1999 | Kaeser |
| 5,966,706 A | 10/1999 | Biliris et al. |
| 5,999,911 A | 12/1999 | Berg et al. |
| 6,006,242 A | 12/1999 | Poole et al. |
| 6,057,757 A | 5/2000 | Arrowsmith et al. |
| 6,065,026 A | 5/2000 | Cornelia et al. |
| 6,094,643 A | 7/2000 | Anderson et al. |
| 6,134,582 A | 10/2000 | Kennedy |
| 6,161,098 A | 12/2000 | Wallman |
| 6,219,053 B1 | 4/2001 | Tachibana et al. |
| 6,232,971 B1 | 5/2001 | Haynes |
| 6,237,138 B1 | 5/2001 | Hameluck et al. |
| 6,243,706 B1 | 6/2001 | Moreau et al. |
| 6,243,717 B1 | 6/2001 | Gordon et al. |
| 6,279,018 B1 | 8/2001 | Kudrolli et al. |
| 6,341,310 B1 | 1/2002 | Leshem et al. |
| 6,369,835 B1 | 4/2002 | Lin |
| 6,370,538 B1 | 4/2002 | Lamping et al. |
| 6,430,305 B1 | 8/2002 | Decker |
| 6,463,404 B1 | 10/2002 | Appleby |
| 6,505,196 B2 | 1/2003 | Drucker et al. |
| 6,519,627 B1 | 2/2003 | Dan et al. |
| 6,523,019 B1 | 2/2003 | Borthwick |
| 6,549,944 B1 | 4/2003 | Weinberg et al. |
| 6,714,936 B1 | 3/2004 | Nevin, III |
| 6,820,135 B1 | 11/2004 | Dingman |
| 6,839,745 B1 | 1/2005 | Dingari et al. |
| 6,944,821 B1 | 9/2005 | Bates et al. |
| 6,978,419 B1 | 12/2005 | Kantrowitz |
| 6,980,984 B1 | 12/2005 | Huffman et al. |
| 7,058,648 B1 | 6/2006 | Lightfoot et al. |
| 7,086,028 B1 | 8/2006 | Davis et al. |
| 7,089,541 B2 | 8/2006 | Ungar |
| 7,139,800 B2 | 11/2006 | Bellotti et al. |
| 7,168,039 B2 | 1/2007 | Bertram |
| 7,171,427 B2 | 1/2007 | Witowski et al. |
| 7,174,377 B2 | 2/2007 | Bernard et al. |
| 7,213,030 B1 | 5/2007 | Jenkins |
| 7,278,105 B1 | 10/2007 | Kitts |
| 7,379,903 B2 | 5/2008 | Caballero et al. |
| 7,383,239 B2 | 6/2008 | Bonissone |
| 7,392,254 B1 | 6/2008 | Jenkins |
| 7,403,942 B1 | 7/2008 | Bayliss |
| 7,418,431 B1 | 8/2008 | Nies et al. |
| 7,426,654 B2 | 9/2008 | Adams et al. |
| 7,441,182 B2 | 10/2008 | Beilinson et al. |
| 7,454,466 B2 | 11/2008 | Bellotti et al. |
| 7,461,158 B2 | 12/2008 | Rider et al. |
| 7,467,375 B2 | 12/2008 | Tondreau et al. |
| 7,525,422 B2 | 4/2009 | Bishop et al. |
| 7,617,232 B2 | 11/2009 | Gabbert et al. |
| 7,627,489 B2 | 12/2009 | Schaeffer et al. |
| 7,627,812 B2 | 12/2009 | Chamberlain et al. |
| 7,634,717 B2 | 12/2009 | Chamberlain et al. |
| 7,703,021 B1 | 4/2010 | Flam |
| 7,716,077 B1 | 5/2010 | Mikurak |
| 7,725,547 B2 | 5/2010 | Albertson et al. |
| 7,756,843 B1 | 7/2010 | Palmer |
| 7,757,220 B2 | 7/2010 | Griffith et al. |
| 7,765,489 B1 | 7/2010 | Shah |
| 7,770,100 B2 | 8/2010 | Chamberlain et al. |
| 7,800,796 B2 | 9/2010 | Saito |
| 7,813,937 B1 | 10/2010 | Pathria et al. |
| 7,818,658 B2 | 10/2010 | Chen |
| 7,827,045 B2 | 11/2010 | Madill et al. |
| 7,877,421 B2 | 1/2011 | Berger et al. |
| 7,880,921 B2 | 2/2011 | Dattilo et al. |
| 7,899,796 B1 | 3/2011 | Borthwick et al. |
| 7,912,842 B1 | 3/2011 | Bayliss |
| 7,917,376 B2 | 3/2011 | Bellin et al. |
| 7,941,321 B2 | 5/2011 | Greenstein et al. |
| 7,941,336 B1 | 5/2011 | Robin-Jan |
| 7,958,147 B1 | 6/2011 | Turner et al. |
| 7,962,495 B2 | 6/2011 | Jain et al. |
| 7,962,848 B2 | 6/2011 | Bertram |
| 7,966,199 B1 | 6/2011 | Frasher |
| 8,001,465 B2 | 8/2011 | Kudrolli et al. |
| 8,001,482 B2 | 8/2011 | Bhattiprolu et al. |
| 8,010,507 B2 | 8/2011 | Poston et al. |
| 8,015,487 B2 | 9/2011 | Roy et al. |
| 8,036,971 B2 | 10/2011 | Aymeloglu et al. |
| 8,046,283 B2 | 10/2011 | Burns |
| 8,054,756 B2 | 11/2011 | Chand et al. |
| 8,073,857 B2 | 12/2011 | Sreekanth |
| 8,117,022 B2 | 2/2012 | Linker |
| 8,126,848 B2 | 2/2012 | Wagner |
| 8,214,232 B2 | 7/2012 | Tyler et al. |
| 8,214,490 B1 | 7/2012 | Vos et al. |
| 8,225,201 B2 | 7/2012 | Michael |
| 8,229,902 B2 | 7/2012 | Vishniac et al. |
| 8,230,333 B2 | 7/2012 | Decherd et al. |
| 8,290,838 B1 | 10/2012 | Thakur et al. |
| 8,301,464 B1 | 10/2012 | Cave et al. |
| 8,302,855 B2 | 11/2012 | Ma et al. |
| 8,364,642 B1 | 1/2013 | Garrod |
| 8,417,715 B1 | 4/2013 | Bruckhaus et al. |
| 8,429,527 B1 | 4/2013 | Arbogast |
| 8,447,722 B1 | 5/2013 | Ahuja et al. |
| 8,473,454 B2 | 6/2013 | Evanitsky et al. |
| 8,484,115 B2 | 7/2013 | Aymeloglu et al. |
| 8,489,623 B2 | 7/2013 | Jain et al. |
| 8,489,641 B1 | 7/2013 | Seefeld et al. |
| 8,514,082 B2 | 8/2013 | Cova et al. |
| 8,515,912 B2 | 8/2013 | Garrod et al. |
| 8,527,461 B2 | 9/2013 | Ducott, III et al. |
| 8,538,827 B1 | 9/2013 | Dryer et al. |
| 8,554,579 B2 | 10/2013 | Tribble et al. |
| 8,554,719 B2 | 10/2013 | McGrew |
| 8,577,911 B1 | 11/2013 | Stepinski et al. |
| 8,578,500 B2 | 11/2013 | Long |
| 8,589,273 B2 | 11/2013 | Creeden et al. |
| 8,600,872 B1 | 12/2013 | Yan |
| 8,601,326 B1 | 12/2013 | Kirn |
| 8,620,641 B2 | 12/2013 | Farnsworth et al. |
| 8,639,522 B2 | 1/2014 | Pathria et al. |
| 8,639,552 B1 | 1/2014 | Chen et al. |
| 8,655,687 B2 | 2/2014 | Zizzamia |
| 8,666,861 B2 | 3/2014 | Li et al. |
| 8,682,696 B1 | 3/2014 | Shanmugam |
| 8,688,573 B1 | 4/2014 | Ruknoic et al. |
| 8,689,108 B1 | 4/2014 | Duffield et al. |
| 8,713,467 B1 | 4/2014 | Goldenberg et al. |
| 8,732,574 B2 | 5/2014 | Burr et al. |
| 8,744,890 B1 | 6/2014 | Bernier |
| 8,798,354 B1 | 8/2014 | Bunzel et al. |
| 8,799,313 B2 | 8/2014 | Satlow |
| 8,812,960 B1 | 8/2014 | Sun et al. |
| 8,903,717 B2 | 12/2014 | Elliot |
| 8,924,388 B2 | 12/2014 | Elliot et al. |
| 8,924,389 B2 | 12/2014 | Elliot et al. |
| 8,938,686 B1 | 1/2015 | Erenrich et al. |
| 8,949,164 B1 | 2/2015 | Mohler |
| 8,972,336 B2 | 3/2015 | Jagota |
| 8,984,390 B2 | 3/2015 | Aymeloglu et al. |
| 9,032,531 B1 | 5/2015 | Scorvo et al. |
| 9,058,315 B2 | 6/2015 | Burr et al. |
| 9,100,428 B1 | 8/2015 | Visbal |
| 9,105,000 B1 | 8/2015 | White et al. |
| 9,129,219 B1 | 9/2015 | Robertson et al. |
| 9,418,337 B1 | 8/2016 | Elser et al. |
| 9,836,580 B2 | 12/2017 | Fendell et al. |
| 2001/0021936 A1 | 9/2001 | Bertram |

(56) References Cited

U.S. PATENT DOCUMENTS

| | | |
|---|---|---|
| 2001/0027424 A1 | 10/2001 | Torigoe |
| 2002/0032677 A1 | 3/2002 | Morgenthaler et al. |
| 2002/0035590 A1 | 3/2002 | Eibach et al. |
| 2002/0065708 A1 | 5/2002 | Senay et al. |
| 2002/0095360 A1 | 7/2002 | Joao |
| 2002/0095658 A1 | 7/2002 | Shulman |
| 2002/0103705 A1 | 8/2002 | Brady |
| 2002/0130907 A1 | 9/2002 | Chi et al. |
| 2002/0147805 A1 | 10/2002 | Leshem et al. |
| 2002/0174201 A1 | 11/2002 | Ramer et al. |
| 2002/0194119 A1* | 12/2002 | Wright ............... G06Q 20/04 705/38 |
| 2003/0033347 A1* | 2/2003 | Bolle ............... G06F 17/30253 718/107 |
| 2003/0036927 A1 | 2/2003 | Bowen |
| 2003/0093401 A1 | 5/2003 | Czahkowski et al. |
| 2003/0093755 A1 | 5/2003 | O'Carroll |
| 2003/0105759 A1 | 6/2003 | Bess et al. |
| 2003/0115481 A1 | 6/2003 | Baird et al. |
| 2003/0126102 A1 | 7/2003 | Borthwick |
| 2003/0163352 A1 | 8/2003 | Surpin et al. |
| 2003/0177112 A1 | 9/2003 | Gardner |
| 2003/0182313 A1 | 9/2003 | Federwisch et al. |
| 2003/0200217 A1 | 10/2003 | Ackerman |
| 2003/0212718 A1 | 11/2003 | Tester |
| 2004/0003009 A1 | 1/2004 | Wilmot |
| 2004/0006523 A1 | 1/2004 | Coker |
| 2004/0034570 A1 | 2/2004 | Davis |
| 2004/0044648 A1 | 3/2004 | Anfindsen et al. |
| 2004/0083466 A1 | 4/2004 | Dapp et al. |
| 2004/0085318 A1 | 5/2004 | Hassler et al. |
| 2004/0088177 A1 | 5/2004 | Travis et al. |
| 2004/0095349 A1 | 5/2004 | Bito et al. |
| 2004/0111480 A1 | 6/2004 | Yue |
| 2004/0117387 A1 | 6/2004 | Civetta et al. |
| 2004/0126840 A1 | 7/2004 | Cheng et al. |
| 2004/0153418 A1 | 8/2004 | Hanweck |
| 2004/0153451 A1 | 8/2004 | Phillips et al. |
| 2004/0181554 A1 | 9/2004 | Heckerman et al. |
| 2004/0205492 A1 | 10/2004 | Newsome |
| 2004/0210763 A1 | 10/2004 | Jonas |
| 2004/0236688 A1 | 11/2004 | Bozeman |
| 2005/0010472 A1 | 1/2005 | Quatse et al. |
| 2005/0028094 A1 | 2/2005 | Allyn |
| 2005/0039116 A1 | 2/2005 | Slack-Smith |
| 2005/0086207 A1 | 4/2005 | Heuer et al. |
| 2005/0091186 A1 | 4/2005 | Elish |
| 2005/0097441 A1 | 5/2005 | Herbach et al. |
| 2005/0108063 A1 | 5/2005 | Madill et al. |
| 2005/0125715 A1 | 6/2005 | Di Franco et al. |
| 2005/0131935 A1 | 6/2005 | O'Leary et al. |
| 2005/0133588 A1 | 6/2005 | Williams |
| 2005/0149455 A1 | 7/2005 | Bruesewitz et al. |
| 2005/0149527 A1 | 7/2005 | Berlin |
| 2005/0154628 A1 | 7/2005 | Eckart et al. |
| 2005/0154769 A1 | 7/2005 | Eckart et al. |
| 2005/0180330 A1 | 8/2005 | Shapiro |
| 2005/0182654 A1 | 8/2005 | Abolfathi et al. |
| 2005/0262512 A1 | 11/2005 | Schmidt et al. |
| 2006/0010130 A1 | 1/2006 | Leff et al. |
| 2006/0026120 A1 | 2/2006 | Carolan et al. |
| 2006/0026170 A1 | 2/2006 | Kreitler et al. |
| 2006/0026561 A1 | 2/2006 | Bauman et al. |
| 2006/0031779 A1 | 2/2006 | Theurer et al. |
| 2006/0045470 A1 | 3/2006 | Poslinski et al. |
| 2006/0053097 A1 | 3/2006 | King et al. |
| 2006/0053170 A1 | 3/2006 | Hill et al. |
| 2006/0059423 A1 | 3/2006 | Lehmann et al. |
| 2006/0074866 A1 | 4/2006 | Chamberlain et al. |
| 2006/0080139 A1 | 4/2006 | Mainzer |
| 2006/0080316 A1 | 4/2006 | Gilmore et al. |
| 2006/0080619 A1 | 4/2006 | Carlson et al. |
| 2006/0129746 A1 | 6/2006 | Porter |
| 2006/0136513 A1 | 6/2006 | Ngo et al. |
| 2006/0142949 A1 | 6/2006 | Helt |
| 2006/0143034 A1 | 6/2006 | Rothermel |
| 2006/0143075 A1 | 6/2006 | Carr et al. |
| 2006/0143079 A1 | 6/2006 | Basak et al. |
| 2006/0149596 A1 | 7/2006 | Surpin et al. |
| 2006/0178915 A1 | 8/2006 | Chao |
| 2006/0218206 A1 | 9/2006 | Bourbonnais et al. |
| 2006/0218491 A1 | 9/2006 | Grossman et al. |
| 2006/0241974 A1 | 10/2006 | Chao et al. |
| 2006/0253502 A1 | 11/2006 | Raman et al. |
| 2006/0265417 A1 | 11/2006 | Amato et al. |
| 2006/0277460 A1 | 12/2006 | Forstall et al. |
| 2007/0000999 A1 | 1/2007 | Kubo et al. |
| 2007/0011304 A1 | 1/2007 | Error |
| 2007/0038646 A1 | 2/2007 | Thota |
| 2007/0043686 A1 | 2/2007 | Teng et al. |
| 2007/0061259 A1 | 3/2007 | Zoldi et al. |
| 2007/0061752 A1 | 3/2007 | Cory |
| 2007/0067285 A1 | 3/2007 | Blume |
| 2007/0106582 A1 | 5/2007 | Baker et al. |
| 2007/0113164 A1 | 5/2007 | Hansen et al. |
| 2007/0136095 A1 | 6/2007 | Weinstein |
| 2007/0150801 A1 | 6/2007 | Chidlovskii et al. |
| 2007/0156673 A1 | 7/2007 | Maga |
| 2007/0168871 A1 | 7/2007 | Jenkins |
| 2007/0178501 A1 | 8/2007 | Rabinowitz et al. |
| 2007/0185867 A1 | 8/2007 | Maga |
| 2007/0192143 A1 | 8/2007 | Krishnan et al. |
| 2007/0233756 A1 | 10/2007 | D'Souza et al. |
| 2007/0239606 A1 | 10/2007 | Eisen |
| 2007/0245339 A1 | 10/2007 | Bauman et al. |
| 2007/0266336 A1 | 11/2007 | Nojima et al. |
| 2007/0271317 A1 | 11/2007 | Carmel |
| 2007/0284433 A1 | 12/2007 | Domenica et al. |
| 2007/0295797 A1 | 12/2007 | Herman et al. |
| 2007/0299697 A1 | 12/2007 | Friedlander et al. |
| 2008/0005063 A1 | 1/2008 | Seeds |
| 2008/0016155 A1 | 1/2008 | Khalatian |
| 2008/0046481 A1 | 2/2008 | Gould et al. |
| 2008/0069081 A1 | 3/2008 | Chand et al. |
| 2008/0077597 A1 | 3/2008 | Butler |
| 2008/0077642 A1 | 3/2008 | Carbone et al. |
| 2008/0091693 A1 | 4/2008 | Murthy |
| 2008/0103798 A1 | 5/2008 | Domenikos et al. |
| 2008/0103996 A1 | 5/2008 | Forman et al. |
| 2008/0109714 A1 | 5/2008 | Kumar et al. |
| 2008/0126344 A1 | 5/2008 | Hoffman et al. |
| 2008/0126951 A1 | 5/2008 | Sood et al. |
| 2008/0140387 A1 | 6/2008 | Linker |
| 2008/0140576 A1 | 6/2008 | Lewis et al. |
| 2008/0155440 A1 | 6/2008 | Trevor et al. |
| 2008/0172257 A1 | 7/2008 | Bisker et al. |
| 2008/0172607 A1 | 7/2008 | Baer |
| 2008/0195417 A1 | 8/2008 | Surpin et al. |
| 2008/0195421 A1 | 8/2008 | Ludwig et al. |
| 2008/0195672 A1 | 8/2008 | Hamel et al. |
| 2008/0222038 A1 | 9/2008 | Eden et al. |
| 2008/0222295 A1 | 9/2008 | Robinson et al. |
| 2008/0228467 A1 | 9/2008 | Womack et al. |
| 2008/0235199 A1 | 9/2008 | Li et al. |
| 2008/0243711 A1 | 10/2008 | Aymeloglu et al. |
| 2008/0249820 A1 | 10/2008 | Pathria |
| 2008/0255973 A1 | 10/2008 | El Wade et al. |
| 2008/0263468 A1 | 10/2008 | Cappione et al. |
| 2008/0267386 A1 | 10/2008 | Cooper |
| 2008/0270316 A1 | 10/2008 | Guidotti et al. |
| 2008/0270438 A1 | 10/2008 | Aronson et al. |
| 2008/0281580 A1 | 11/2008 | Zabokritski |
| 2008/0281819 A1 | 11/2008 | Tenenbaum et al. |
| 2008/0301042 A1 | 12/2008 | Patzer |
| 2008/0313132 A1 | 12/2008 | Hao et al. |
| 2008/0313243 A1 | 12/2008 | Poston et al. |
| 2009/0018996 A1 | 1/2009 | Hunt et al. |
| 2009/0031401 A1 | 1/2009 | Cudich et al. |
| 2009/0043801 A1 | 2/2009 | LeClair |
| 2009/0055208 A1 | 2/2009 | Kaiser |
| 2009/0055487 A1 | 2/2009 | Moraes et al. |
| 2009/0070162 A1 | 3/2009 | Leonelli et al. |
| 2009/0076845 A1 | 3/2009 | Bellin et al. |
| 2009/0089651 A1 | 4/2009 | Herberger et al. |

(56) References Cited

U.S. PATENT DOCUMENTS

| | | |
|---|---|---|
| 2009/0094166 A1 | 4/2009 | Aymeloglu et al. |
| 2009/0106178 A1 | 4/2009 | Chu |
| 2009/0106242 A1 | 4/2009 | McGrew |
| 2009/0112678 A1 | 4/2009 | Luzardo |
| 2009/0112745 A1 | 4/2009 | Stefanescu |
| 2009/0125359 A1 | 5/2009 | Knapic |
| 2009/0125459 A1 | 5/2009 | Norton et al. |
| 2009/0132953 A1 | 5/2009 | Reed et al. |
| 2009/0150868 A1 | 6/2009 | Chakra et al. |
| 2009/0164387 A1 | 6/2009 | Armstrong et al. |
| 2009/0164934 A1 | 6/2009 | Bhattiprolu et al. |
| 2009/0177492 A1 | 7/2009 | Hasan et al. |
| 2009/0187546 A1 | 7/2009 | Whyte et al. |
| 2009/0187548 A1 | 7/2009 | Ji et al. |
| 2009/0198518 A1 | 8/2009 | McKenzie et al. |
| 2009/0199106 A1 | 8/2009 | Jonsson et al. |
| 2009/0216562 A1 | 8/2009 | Faulkner et al. |
| 2009/0222287 A1 | 9/2009 | Legorreta et al. |
| 2009/0228365 A1 | 9/2009 | Tomchek et al. |
| 2009/0240529 A1 | 9/2009 | Chess et al. |
| 2009/0248757 A1 | 10/2009 | Havewala et al. |
| 2009/0249244 A1 | 10/2009 | Robinson et al. |
| 2009/0271343 A1 | 10/2009 | Vaiciulis et al. |
| 2009/0281839 A1 | 11/2009 | Lynn et al. |
| 2009/0287470 A1 | 11/2009 | Farnsworth et al. |
| 2009/0299830 A1 | 12/2009 | West et al. |
| 2009/0307049 A1 | 12/2009 | Elliott et al. |
| 2009/0313311 A1 | 12/2009 | Hoffmann et al. |
| 2009/0313463 A1 | 12/2009 | Pang et al. |
| 2009/0319418 A1 | 12/2009 | Herz |
| 2009/0319891 A1 | 12/2009 | MacKinlay |
| 2010/0030722 A1 | 2/2010 | Goodson et al. |
| 2010/0031141 A1 | 2/2010 | Summers et al. |
| 2010/0042922 A1 | 2/2010 | Bradateanu et al. |
| 2010/0057622 A1 | 3/2010 | Faith et al. |
| 2010/0070531 A1 | 3/2010 | Aymeloglu et al. |
| 2010/0070842 A1 | 3/2010 | Aymeloglu et al. |
| 2010/0070844 A1 | 3/2010 | Aymeloglu et al. |
| 2010/0070897 A1 | 3/2010 | Aymeloglu et al. |
| 2010/0082369 A1 | 4/2010 | Prenelus et al. |
| 2010/0082541 A1 | 4/2010 | Kottomtharayil |
| 2010/0082671 A1 | 4/2010 | Li et al. |
| 2010/0094765 A1 | 4/2010 | Nandy |
| 2010/0098318 A1 | 4/2010 | Anderson |
| 2010/0114817 A1 | 5/2010 | Broeder et al. |
| 2010/0114887 A1 | 5/2010 | Conway et al. |
| 2010/0122152 A1 | 5/2010 | Chamberlain et al. |
| 2010/0131502 A1 | 5/2010 | Fordham |
| 2010/0145909 A1 | 6/2010 | Ngo |
| 2010/0161735 A1 | 6/2010 | Sharma |
| 2010/0169192 A1 | 7/2010 | Zoldi et al. |
| 2010/0191563 A1 | 7/2010 | Schlaifer et al. |
| 2010/0204983 A1 | 8/2010 | Chung et al. |
| 2010/0223260 A1 | 9/2010 | Wu |
| 2010/0235915 A1 | 9/2010 | Memon et al. |
| 2010/0262688 A1 | 10/2010 | Hussain et al. |
| 2010/0280851 A1 | 11/2010 | Merkin |
| 2010/0293174 A1 | 11/2010 | Bennett et al. |
| 2010/0306285 A1 | 12/2010 | Shah et al. |
| 2010/0306713 A1 | 12/2010 | Geisner et al. |
| 2010/0312837 A1 | 12/2010 | Bodapati et al. |
| 2010/0313239 A1 | 12/2010 | Chakra et al. |
| 2010/0324929 A1 | 12/2010 | Petrasich et al. |
| 2010/0325581 A1 | 12/2010 | Finkelstein et al. |
| 2011/0004626 A1 | 1/2011 | Naeymi-Rad et al. |
| 2011/0047159 A1 | 2/2011 | Baid et al. |
| 2011/0055074 A1 | 3/2011 | Chen et al. |
| 2011/0060753 A1 | 3/2011 | Shaked et al. |
| 2011/0061013 A1 | 3/2011 | Bilicki et al. |
| 2011/0066497 A1 | 3/2011 | Gopinath et al. |
| 2011/0078173 A1 | 3/2011 | Seligmann et al. |
| 2011/0093327 A1 | 4/2011 | Fordyce et al. |
| 2011/0099133 A1 | 4/2011 | Chang et al. |
| 2011/0099628 A1 | 4/2011 | Lanxner et al. |
| 2011/0131122 A1 | 6/2011 | Griffin et al. |
| 2011/0153384 A1 | 6/2011 | Horne et al. |
| 2011/0161409 A1 | 6/2011 | Nair |
| 2011/0167105 A1 | 7/2011 | Ramakrishnan et al. |
| 2011/0173093 A1 | 7/2011 | Psota et al. |
| 2011/0179048 A1 | 7/2011 | Satlow |
| 2011/0208565 A1 | 8/2011 | Ross et al. |
| 2011/0208724 A1 | 8/2011 | Jones et al. |
| 2011/0208822 A1 | 8/2011 | Rathod |
| 2011/0213655 A1 | 9/2011 | Henkin |
| 2011/0218955 A1 | 9/2011 | Tang |
| 2011/0225482 A1 | 9/2011 | Chan et al. |
| 2011/0225586 A1 | 9/2011 | Bentley et al. |
| 2011/0231305 A1 | 9/2011 | Winters |
| 2011/0246229 A1 | 10/2011 | Pacha |
| 2011/0252282 A1 | 10/2011 | Meek et al. |
| 2011/0258216 A1 | 10/2011 | Supakkul et al. |
| 2011/0270604 A1 | 11/2011 | Qi et al. |
| 2011/0270834 A1 | 11/2011 | Sokolan et al. |
| 2011/0289397 A1 | 11/2011 | Eastmond et al. |
| 2011/0291851 A1 | 12/2011 | Whisenant |
| 2011/0295649 A1 | 12/2011 | Fine |
| 2011/0307382 A1 | 12/2011 | Siegel et al. |
| 2011/0310005 A1 | 12/2011 | Chen et al. |
| 2011/0314007 A1 | 12/2011 | Dassa et al. |
| 2011/0314024 A1 | 12/2011 | Chang et al. |
| 2012/0004894 A1 | 1/2012 | Butler |
| 2012/0011238 A1 | 1/2012 | Rathod |
| 2012/0011245 A1 | 1/2012 | Gillette et al. |
| 2012/0013684 A1 | 1/2012 | Robertson et al. |
| 2012/0019559 A1 | 1/2012 | Siler et al. |
| 2012/0022945 A1 | 1/2012 | Falkenborg et al. |
| 2012/0036434 A1 | 2/2012 | Oberstein |
| 2012/0054284 A1 | 3/2012 | Rakshit |
| 2012/0059853 A1 | 3/2012 | Jagota |
| 2012/0065987 A1 | 3/2012 | Farooq et al. |
| 2012/0066166 A1 | 3/2012 | Curbera et al. |
| 2012/0078595 A1 | 3/2012 | Balandin et al. |
| 2012/0079363 A1 | 3/2012 | Folting et al. |
| 2012/0084117 A1 | 4/2012 | Tavares et al. |
| 2012/0084184 A1 | 4/2012 | Raleigh |
| 2012/0084287 A1 | 4/2012 | Lakshminarayan et al. |
| 2012/0131512 A1 | 5/2012 | Takeuchi et al. |
| 2012/0144335 A1 | 6/2012 | Abeln et al. |
| 2012/0158585 A1 | 6/2012 | Ganti |
| 2012/0159362 A1 | 6/2012 | Brown et al. |
| 2012/0173381 A1 | 7/2012 | Smith |
| 2012/0188252 A1 | 7/2012 | Law |
| 2012/0191446 A1 | 7/2012 | Binsztok et al. |
| 2012/0196558 A1 | 8/2012 | Reich et al. |
| 2012/0197657 A1 | 8/2012 | Prodanovic |
| 2012/0197660 A1 | 8/2012 | Prodanovic |
| 2012/0215784 A1 | 8/2012 | King et al. |
| 2012/0221553 A1 | 8/2012 | Wittmer et al. |
| 2012/0221580 A1 | 8/2012 | Barney |
| 2012/0226523 A1 | 9/2012 | Weiss |
| 2012/0226590 A1 | 9/2012 | Love et al. |
| 2012/0245976 A1 | 9/2012 | Kumar et al. |
| 2012/0246148 A1 | 9/2012 | Dror |
| 2012/0278249 A1 | 11/2012 | Duggal et al. |
| 2012/0310661 A1 | 12/2012 | Greene |
| 2012/0323888 A1 | 12/2012 | Osann, Jr. |
| 2012/0330973 A1 | 12/2012 | Ghuneim et al. |
| 2013/0006655 A1 | 1/2013 | Van Arkel et al. |
| 2013/0006668 A1 | 1/2013 | Van Arkel et al. |
| 2013/0016106 A1 | 1/2013 | Yip et al. |
| 2013/0046842 A1 | 2/2013 | Muntz et al. |
| 2013/0054306 A1 | 2/2013 | Bhalla |
| 2013/0057551 A1 | 3/2013 | Ebert et al. |
| 2013/0061169 A1 | 3/2013 | Pearcy et al. |
| 2013/0073377 A1 | 3/2013 | Heath |
| 2013/0096968 A1 | 4/2013 | Van Pelt et al. |
| 2013/0096988 A1 | 4/2013 | Grossman et al. |
| 2013/0097130 A1 | 4/2013 | Bingol et al. |
| 2013/0097482 A1 | 4/2013 | Marantz et al. |
| 2013/0110746 A1 | 5/2013 | Ahn |
| 2013/0117081 A1* | 5/2013 | Wilkins ............ G06Q 30/0248 705/14.4 |
| 2013/0124193 A1 | 5/2013 | Holmberg |
| 2013/0132348 A1 | 5/2013 | Garrod |

(56) References Cited

U.S. PATENT DOCUMENTS

| | | |
|---|---|---|
| 2013/0151453 A1 | 6/2013 | Bhanot et al. |
| 2013/0166348 A1 | 6/2013 | Scotto |
| 2013/0166480 A1 | 6/2013 | Popescu et al. |
| 2013/0185245 A1 | 7/2013 | Anderson |
| 2013/0185307 A1 | 7/2013 | El-Yaniv et al. |
| 2013/0224696 A1 | 8/2013 | Wolfe et al. |
| 2013/0226318 A1 | 8/2013 | Procyk |
| 2013/0226944 A1 | 8/2013 | Baid et al. |
| 2013/0238616 A1 | 9/2013 | Rose et al. |
| 2013/0238664 A1 | 9/2013 | Hsu et al. |
| 2013/0246170 A1 | 9/2013 | Gross et al. |
| 2013/0246537 A1 | 9/2013 | Gaddala |
| 2013/0246597 A1 | 9/2013 | Iizawa et al. |
| 2013/0262328 A1 | 10/2013 | Federgreen |
| 2013/0262527 A1 | 10/2013 | Hunter et al. |
| 2013/0263019 A1 | 10/2013 | Castellanos et al. |
| 2013/0276799 A1 | 10/2013 | Davidson |
| 2013/0282696 A1 | 10/2013 | John et al. |
| 2013/0290011 A1 | 10/2013 | Lynn et al. |
| 2013/0290825 A1 | 10/2013 | Arndt et al. |
| 2013/0297619 A1 | 11/2013 | Chandrasekaran et al. |
| 2013/0304770 A1 | 11/2013 | Boero et al. |
| 2013/0325826 A1 | 12/2013 | Agarwal et al. |
| 2014/0006404 A1 | 1/2014 | McGrew et al. |
| 2014/0012724 A1 | 1/2014 | O'Leary et al. |
| 2014/0012796 A1 | 1/2014 | Petersen et al. |
| 2014/0019936 A1 | 1/2014 | Cohanoff |
| 2014/0032506 A1 | 1/2014 | Hoey et al. |
| 2014/0033010 A1 | 1/2014 | Richardt et al. |
| 2014/0040371 A1 | 2/2014 | Gurevich et al. |
| 2014/0052466 A1 | 2/2014 | DeVille et al. |
| 2014/0058754 A1 | 2/2014 | Wild |
| 2014/0058763 A1* | 2/2014 | Zizzamia ............... G06Q 40/08 705/4 |
| 2014/0058914 A1 | 2/2014 | Song et al. |
| 2014/0068487 A1 | 3/2014 | Steiger et al. |
| 2014/0081652 A1* | 3/2014 | Klindworth ............ G06Q 10/10 705/2 |
| 2014/0095363 A1 | 4/2014 | Caldwell |
| 2014/0095509 A1 | 4/2014 | Patton |
| 2014/0108074 A1 | 4/2014 | Miller et al. |
| 2014/0108380 A1 | 4/2014 | Gotz et al. |
| 2014/0108985 A1 | 4/2014 | Scott et al. |
| 2014/0123279 A1 | 5/2014 | Bishop et al. |
| 2014/0129936 A1 | 5/2014 | Richards et al. |
| 2014/0136237 A1 | 5/2014 | Anderson et al. |
| 2014/0136285 A1 | 5/2014 | Carvalho |
| 2014/0143009 A1 | 5/2014 | Brice et al. |
| 2014/0149130 A1 | 5/2014 | Getchius |
| 2014/0156527 A1 | 6/2014 | Grigg et al. |
| 2014/0157172 A1 | 6/2014 | Peery et al. |
| 2014/0164502 A1 | 6/2014 | Khodorenko et al. |
| 2014/0189536 A1 | 7/2014 | Lange et al. |
| 2014/0195515 A1 | 7/2014 | Baker et al. |
| 2014/0214579 A1 | 7/2014 | Shen et al. |
| 2014/0222521 A1 | 8/2014 | Chait |
| 2014/0222752 A1 | 8/2014 | Isman et al. |
| 2014/0222793 A1 | 8/2014 | Sadkin et al. |
| 2014/0229554 A1 | 8/2014 | Grunin et al. |
| 2014/0244284 A1 | 8/2014 | Smith |
| 2014/0278339 A1* | 9/2014 | Aliferis ................ G06N 99/005 703/22 |
| 2014/0278479 A1 | 9/2014 | Wang et al. |
| 2014/0282177 A1 | 9/2014 | Wang et al. |
| 2014/0344230 A1 | 11/2014 | Krause et al. |
| 2014/0358789 A1 | 12/2014 | Boding et al. |
| 2014/0358829 A1 | 12/2014 | Hurwitz |
| 2014/0366132 A1 | 12/2014 | Stiansen et al. |
| 2015/0012509 A1 | 1/2015 | Kirn |
| 2015/0046481 A1 | 2/2015 | Elliot |
| 2015/0073929 A1 | 3/2015 | Psota et al. |
| 2015/0073954 A1 | 3/2015 | Braff |
| 2015/0085997 A1 | 3/2015 | Biage et al. |
| 2015/0095773 A1 | 4/2015 | Gonsalves et al. |
| 2015/0100897 A1 | 4/2015 | Sun et al. |
| 2015/0106379 A1 | 4/2015 | Elliot et al. |
| 2015/0134512 A1 | 5/2015 | Mueller |
| 2015/0135256 A1 | 5/2015 | Hoy et al. |
| 2015/0161611 A1 | 6/2015 | Duke et al. |
| 2015/0186821 A1 | 7/2015 | Wang et al. |
| 2015/0187036 A1 | 7/2015 | Wang et al. |
| 2015/0188872 A1 | 7/2015 | White |
| 2015/0235334 A1 | 8/2015 | Wang et al. |
| 2015/0254220 A1 | 9/2015 | Burr et al. |
| 2015/0269316 A1 | 9/2015 | Hussam |
| 2015/0269334 A1 | 9/2015 | Fendell et al. |
| 2015/0338233 A1 | 11/2015 | Cervelli et al. |
| 2015/0379413 A1 | 12/2015 | Robertson et al. |
| 2016/0004764 A1 | 1/2016 | Chakerian et al. |
| 2016/0034578 A1 | 2/2016 | Wang et al. |

FOREIGN PATENT DOCUMENTS

| | | |
|---|---|---|
| CN | 102054015 | 5/2014 |
| DE | 102014103476 | 9/2014 |
| DE | 102014204827 | 9/2014 |
| DE | 102014204830 | 9/2014 |
| DE | 102014204834 | 9/2014 |
| DE | 102014213036 | 1/2015 |
| EP | 1672527 | 6/2006 |
| EP | 1840523 | 3/2011 |
| EP | 2487610 | 8/2012 |
| EP | 2778913 | 9/2014 |
| EP | 2778914 | 9/2014 |
| EP | 2858018 | 4/2015 |
| EP | 2869211 | 5/2015 |
| EP | 2889814 | 7/2015 |
| EP | 2892197 | 7/2015 |
| EP | 2963595 | 1/2016 |
| EP | 2980748 | 2/2016 |
| GB | 2366498 | 3/2002 |
| GB | 2513472 | 10/2014 |
| GB | 2513721 | 11/2014 |
| GB | 2514239 | 11/2014 |
| GB | 2517582 | 2/2015 |
| NL | 2013134 | 1/2015 |
| WO | WO 01/025906 | 4/2001 |
| WO | WO 2001/088750 | 11/2001 |
| WO | WO 2005/116851 | 12/2005 |
| WO | WO 2008/113059 | 9/2008 |
| WO | WO 2009/051987 | 4/2009 |
| WO | WO 2009/061501 | 5/2009 |
| WO | WO 2010/030913 | 3/2010 |
| WO | WO 2010/030914 | 3/2010 |
| WO | WO 2010/030919 | 3/2010 |
| WO | WO 2012/119008 | 9/2012 |

OTHER PUBLICATIONS

Appacts, "Smart Thinking for Super Apps," http://www.appacts.com Printed Jul. 18, 2013 in 4 pages.

Apsalar, "Data Powered Mobile Advertising," "Free Mobile App Analytics" and various analytics related screen shots http://apsalar.com Printed Jul. 18, 2013 in 8 pages.

Capptain—Pilot Your Apps, http://www.capptain.com Printed Jul. 18, 2013 in 6 pages.

Celik, Tantek, "CSS Basic User Interface Module Level 3 (CSSS3 UI)," Section 8 Resizing and Overflow, Jan. 17, 2012, retrieved from internet http://www.w3.org/TR/2012/WD-css3-ui-20120117/#resizing-amp-overflow retrieved on May 18, 2015.

Chaudhuri et al., "An Overview of Business Intelligence Technology," Communications of the ACM, Aug. 2011, vol. 54, No. 8.

Cohn, et al., "Semi-supervised clustering with user feedback," Constrained Clustering: Advances in Algorithms, Theory, and Applications 4.1 (2003): 17-32.

Countly Mobile Analytics, http://count.ly/ Printed Jul. 18, 2013 in 9 pages.

Distimo—App Analytics, http://www.distimo.com/app-analytics Printed Jul. 18, 2013 in 5 pages.

Flurry Analytics, http://www.flurry.com/ Printed Jul. 18, 2013 in 14 pages.

(56) References Cited

OTHER PUBLICATIONS

Google Analytics Official Website—Web Analytics & Reporting, http://www.google.com/analytics.index.html Printed Jul. 18, 2013 in 22 pages.
Gorr et al., "Crime Hot Spot Forecasting: Modeling and Comparative Evaluation", Grant 98-IJ-CX-K005, May 6, 2002, 37 pages.
Gu et al., "Record Linkage: Current Practice and Future Directions," Jan. 15, 2004, pp. 32.
Hansen et al., "Analyzing Social Media Networks with NodeXL: Insights from a Connected World", Chapter 4, pp. 53-67 and Chapter 10, pp. 143-164, published Sep. 2010.
Hua et al., "A Multi-attribute Data Structure with Parallel Bloom Filters for Network Services", HiPC 2006, LNCS 4297, pp. 277-288, 2006.
"HunchLab: Heat Map and Kernel Density Calculation for Crime Analysis," Azavea Journal, printed from www.azavea.com/blogs/newsletter/v4i4/kernel-density-capabilities-added-to-hunchlab/ on Sep. 9, 2014, 2 pages.
Keylines.com, "An Introduction to KeyLines and Network Visualization," Mar. 2014, http://keylines.com/wp-content/uploads/2014/03/Keylines-White-Paper.pdf downloaded May 12, 2014 in 8 pages.
Keylines.com, "KeyLines Datasheet," Mar. 2014, http://keylines.com/wp-content/uploads/2014/03/KeyLines-datasheet.pdf downloaded May 12, 2014 in 2 pages.
Keylines.com, "Visualizing Threats: Improved Cyber Security Through Network Visualization," Apr. 2014, http://keylines.com/wp-content/uploads/2014/04/Visualizing-Threats1.pdf downloaded May 12, 2014 in 10 pages.
Kontagent Mobile Analytics, http://www.kontagent.com/ Printed Jul. 18, 2013 in 9 pages.
Localytics—Mobile App Marketing & Analytics, http://www.localytics.com/ Printed Jul. 18, 2013 in 12 pages.
Manno et al., "Introducing Collaboration in Single-user Applications through the Centralized Control Architecture," 2010, pp. 10.
Mixpanel—Mobile Analytics, https://mixpanel.com/ Printed Jul. 18, 2013 in 13 pages.
Open Web Analytics (OWA), http://www.openwebanalytics.com/ Printed Jul. 19, 2013 in 5 pages.
Piwik—Free Web Analytics Software. http://piwik.org/ Printed Jul. 19, 2013 in18 pages.
"Refresh CSS Ellipsis When Resizing Container—Stack Overflow," Jul. 31, 2013, retrieved from internet http://stackoverflow.com/questions/17964681/refresh-css-ellipsis-when-resizing-container, retrieved on May 18, 2015.
Sigrist, et al., "PROSITE, a protein domain database for functional characterization and annotation," Nucleic Acids Research 38.suppl 1 (2010): D161-D166.
StatCounter—Free Invisible Web Tracker, Hit Counter and Web Stats, http://statcounter.com/ Printed Jul. 19, 2013 in 17 pages.
TestFlight—Beta Testing on the Fly, http://testflightapp.com/ Printed Jul. 18, 2013 in 3 pages.
Trak.io, http://trak.io/ printed Jul. 18, 2013 in 3 pages.
UserMetrix, http://usermetrix.com/android-analytics printed Jul. 18, 2013 in 3 pages.
Valentini et al., "Ensembles of Learning Machines", M. Marinaro and R. Tagliaferri (Eds.): WIRN VIETRI 2002, LNCS 2486, pp. 3-20.
Vose et al., "Help File for ModelRisk Version 5," 2007, Vose Software, pp. 349-353. [Uploaded in 2 Parts].
Wang et al., "Research on a Clustering Data De-Duplication Mechanism Based on Bloom Filter," IEEE 2010, 5 pages.
Wikipedia, "Multimap," Jan. 1, 2013, http://en.wikipedia.org/w/index.php?title=Multimap&oldid=530800748.
Notice of Allowance for U.S. Appl. No. 14/225,084 dated May 4, 2015.
Notice of Allowance for U.S. Appl. No. 14/319,161 dated May 4, 2015.
Notice of Allowance for U.S. Appl. No. 14/323,935 dated Oct. 1, 2015.
Notice of Allowance for U.S. Appl. No. 14/479,863 dated Mar. 31, 2015.
Notice of Allowance for U.S. Appl. No. 14/552,336 dated Nov. 3, 2015.
Notice of Allowance for U.S. Appl. No. 14/746,671 dated Jan. 21, 2016.
Notice of Allowance for U.S. Appl. No. 14/923,364 dated May 6, 2016.
Official Communication for European Patent Application No. 14187996.5 dated Feb. 12, 2015.
Official Communication for European Patent Application No. 14191540.5 dated May 27, 2015.
Official Communication for European Patent Application No. 14200246.8 dated May 29, 2015.
Official Communication for European Patent Application No. 14200298.9 dated May 13, 2015.
Official Communication for European Patent Application No. 15181419.1 dated Sep. 29, 2015.
Official Communication for European Patent Application No. 15184764.7 dated Dec. 14, 2015.
Official Communication for Great Britain Patent Application No. 1404486.1 dated May 21, 2015.
Official Communication for Great Britain Patent Application No. 1404489.5 dated May 21, 2015.
Official Communication for Great Britain Patent Application No. 1404499.4 dated Jun. 11, 2015.
Official Communication for Netherlands Patent Application No. 2012417 dated Sep. 18, 2015.
Official Communication for Netherlands Patent Application No. 2012421 dated Sep. 18, 2015.
Official Communication for Netherlands Patent Application No. 2012438 dated Sep. 21, 2015.
Official Communication for New Zealand Patent Application No. 622473 dated Jun. 19, 2014.
Official Communication for New Zealand Patent Application No. 622473 dated Mar. 27, 2014.
Official Communication for New Zealand Patent Application No. 622513 dated Apr. 3, 2014.
Official Communication for New Zealand Patent Application No. 628161 dated Aug. 25, 2014.
Official Communication for Great Britain Patent Application No. 1404486.1 dated Aug. 27, 2014.
Official Communication for Great Britain Patent Application No. 1404489.5 dated Aug. 27, 2014.
Official Communication for Great Britain Patent Application No. 1404499.4 dated Aug. 20, 2014.
Official Communication for U.S. Appl. No. 13/827,491 dated Dec. 1, 2014.
Official Communication for U.S. Appl. No. 13/827,491 dated Jun. 22, 2015.
Official Communication for U.S. Appl. No. 13/827,491 dated Mar. 30, 2016.
Official Communication for U.S. Appl. No. 13/827,491 dated Oct. 9, 2015.
Official Communication for U.S. Appl. No. 14/141,252 dated Oct. 8, 2015.
Official Communication for U.S. Appl. No. 14/225,006 dated Sep. 10, 2014.
Official Communication for U.S. Appl. No. 14/225,006 dated Sep. 2, 2015.
Official Communication for U.S. Appl. No. 14/225,006 dated Dec. 21, 2015.
Official Communication for U.S. Appl. No. 14/225,006 dated Feb. 27, 2015.
Official Communication for U.S. Appl. No. 14/225,084 dated Sep. 11, 2015.
Official Communication for U.S. Appl. No. 14/225,084 dated Sep. 2, 2014.
Official Communication for U.S. Appl. No. 14/225,084 dated Feb. 20, 2015.
Official Communication for U.S. Appl. No. 14/225,084 dated Jan. 4, 2016.

(56) References Cited

OTHER PUBLICATIONS

Official Communication for U.S. Appl. No. 14/225,160 dated Feb. 11, 2015.
Official Communication for U.S. Appl. No. 14/225,160 dated Aug. 12, 2015.
Official Communication for U.S. Appl. No. 14/225,160 dated May 20, 2015.
Official Communication for U.S. Appl. No. 14/225,160 dated Oct. 22, 2014.
Official Communication for U.S. Appl. No. 14/225,160 dated Jul. 29, 2014.
Official Communication for U.S. Appl. No. 14/306,138 dated Dec. 24, 2015.
Official Communication for U.S. Appl. No. 14/306,138 dated Dec. 3, 2015.
Official Communication for U.S. Appl. No. 14/306,147 dated Dec. 24, 2015.
Official Communication for U.S. Appl. No. 14/319,161 dated Jan. 23, 2015.
Official Communication for U.S. Appl. No. 14/451,221 dated Oct. 21, 2014.
Official Communication for U.S. Appl. No. 14/463,615 dated Sep. 10, 2015.
Official Communication for U.S. Appl. No. 14/463,615 dated Nov. 13, 2014.
Official Communication for U.S. Appl. No. 14/463,615 dated May 21, 2015.
Official Communication for U.S. Appl. No. 14/463,615 dated Jan. 28, 2015.
Official Communication for U.S. Appl. No. 14/463,615 dated Dec. 9, 2015.
Official Communication for U.S. Appl. No. 14/479,863 dated Dec. 26, 2014.
Official Communication for U.S. Appl. No. 14/483,527 dated Jun. 22, 2015.
Official Communication for U.S. Appl. No. 14/483,527 dated Jan. 28, 2015.
Official Communication for U.S. Appl. No. 14/483,527 dated Oct. 28, 2015.
Official Communication for U.S. Appl. No. 14/516,386 dated Feb. 24, 2016.
Official Communication for U.S. Appl. No. 14/552,336 dated Jul. 20, 2015.
Official Communication for U.S. Appl. No. 14/562,524 dated Nov. 10, 2015.
Official Communication for U.S. Appl. No. 14/562,524 dated Sep. 14, 2015.
Official Communication for U.S. Appl. No. 14/571,098 dated Nov. 10, 2015.
Official Communication for U.S. Appl. No. 14/571,098 dated Mar. 11, 2015.
Official Communication for U.S. Appl. No. 14/571,098 dated Aug. 24, 2015.
Official Communication for U.S. Appl. No. 14/571,098 dated Aug. 5, 2015.
Official Communication for U.S. Appl. No. 14/631,633 dated Sep. 10, 2015.
Official Communication for U.S. Appl. No. 14/676,621 dated Oct. 29, 2015.
Official Communication for U.S. Appl. No. 14/676,621 dated Jul. 30, 2015.
Official Communication for U.S. Appl. No. 14/746,671 dated Nov. 12, 2015.
Official Communication for U.S. Appl. No. 14/800,447 dated Dec. 10. 2015.
Official Communication for U.S. Appl. No. 14/813,749 dated Sep. 28, 2015.
Official Communication for U.S. Appl. No. 14/842,734 dated Nov. 19, 2015.
Official Communication for U.S. Appl. No. 14/923,374 dated Feb. 9, 2016.
Official Communication for U.S. Appl. No. 15/017,324 dated Apr. 22, 2016.
"A Tour of Pinboard," <http://pinboard.in/tour> as printed May 15, 2014 in 6 pages.
Abbey, Kristen, "Review of Google Docs," May 1, 2007, pp. 2.
Acklen, Laura, "Absolute Beginner's Guide to Microsoft Word 2003," Dec. 24, 2003, pp. 15-18, 34-41, 308-316.
Adams et al., "Worklets: A Service-Oriented Implementation of Dynamic Flexibility in Workflows," R. Meersman, Z. Tari et al. (Eds.): OTM 2006, LNCS, 4275, pp. 291-308, 2006.
Ananiev et al., "The New Modality API," http://web.archive.org/web/20061211011958/http://java.sun.com/developer/technicalArticles/J2SE/Desktop/javase6/modality/ Jan. 21, 2006, pp. 8.
Anonymous, "A Real-World Problem of Matching Records," Nov. 2006, <http://grupoweb.upf.es/bd-web/slides/ullman.pdf> pp. 1-16.
Bluttman et al., "Excel Formulas and Functions for Dummies," 2005, Wiley Publishing, Inc., pp. 280, 284-286.
Bugzilla@Mozilla, "Bug 18726—[feature] Long-click means of invoking contextual menus not supported," http://bugzilla.mozilla.org/show_bug.cgi?id=18726 printed Jun. 13, 2013 in 11 pages.
Chen et al., "Bringing Order to the Web: Automatically Categorizing Search Results," CHI 2000, Proceedings of the SIGCHI Conference on Human Factors in Computing Systems, Apr. 1-6, 2000, The Hague, The Netherlands, pp. 145-152.
Conner, Nancy, "Google Apps: The Missing Manual," May 1, 2008, pp. 15.
Definition "Identify", downloaded Jan. 22, 2015, 1 page.
Definition "Overlay", downloaded Jan. 22, 2015, 1 page.
Delicious, <http://delicious.com/> as printed May 15, 2014 in 1 page.
Dramowicz, Ela, "Retail Trade Area Analysis Using the Huff Model," Directions Magazine, Jul. 2, 2005 in 10 pages, http://www.directionsmag.com/articles/retail-trade-area-analysis-using-the-huff-model/123411.
"E-MailRelay," <http://web.archive.org/web/20080821175021/http://emailrelay.sourceforge.net/> Aug. 21, 2008, pp. 2.
Galliford, Miles, "SnagIt Versus Free Screen Capture Software: Critical Tools for Website Owners," <http://www.subhub.com/articles/free-screen-capture-software>, Mar. 27, 2008, pp. 11.
GIS-NET 3 Public _ Department of Regional Planning. Planning & Zoning Information for Unincorporated LA County. Retrieved Oct. 2, 2013 from http://gis.planning.lacounty.gov/GIS-NET3_Public/Viewer.html.
"GrabUp—What a Timesaver!" <http://atlchris.com/191/grabup/>, Aug. 11, 2008, pp. 3.
Griffith, Daniel A., "A Generalized Huff Model," Geographical Analysis, Apr. 1982, vol. 14, No. 2, pp. 135-144.
Hibbert et al., "Prediction of Shopping Behavior Using a Huff Model Within a GIS Framework," Healthy Eating in Context, Mar. 18, 2011, pp. 16.
Huff et al., "Calibrating the Huff Model Using ArcGIS Business Analyst," ESRI, Sep. 2008, pp. 33.
Huff, David L., "Parameter Estimation in the Huff Model," ESRI, ArcUser, Oct.-Dec. 2003, pp. 34-36.
JetScreenshot.com, "Share Screenshots via Internet in Seconds," <http://web.archive.org/web/20130807164204/http://www.jetscreenshot.com/>, Aug. 7, 2013, pp. 1.
Johnson, Maggie "Introduction to YACC and Bison", Handout 13, Jul. 8, 2005, in 11 pages.
Johnson, Steve, "Access 2013 on demand," Access 2013 on Demand, May 9, 2013, Que Publishing.
Jul. 2015 Update Appendix 1: Examples published by the USPTO, 22 pages.
Kwout, <http://web.archive.org/web/20080905132448/http://www.kwout.com/> Sep. 5, 2008, pp. 2.
Lim et al., "Resolving Attribute Incompatibility in Database Integration: An Evidential Reasoning Approach," Department of Computer Science, University of Minnesota, 1994, <http://reference.kfupm.edu.sa/content/r/e/resolving_attribute_incompatibility_in_d_531691.pdf> pp. 1-10.

(56) References Cited

OTHER PUBLICATIONS

Litwin et al., "Multidatabase Interoperability," IEEE Computer, Dec. 1986, vol. 19, No. 12, http://www.lamsade.dauphine.fr/~litwin/mdb-interoperability.pdf, pp. 10-18.

Liu, Tianshun, "Combining GIS and the Huff Model to Analyze Suitable Locations for a New Asian Supermarket in the Minneapolis and St. Paul, Minnesota USA," Papers in Resource Analysis, 2012, vol. 14, pp. 8.

Madden, Tom, "Chapter 16: The BLAST Sequence Analysis Tool," The NCBI Handbook, Oct. 2002, pp. 1-15.

Manske, "File Saving Dialogs," <http://www.mozilla.org/editor/ui_specs/FileSaveDialogs.html>, Jan. 20, 1999, pp. 7.

Map of San Jose, CA. Retrieved Oct. 2, 2013 from http://maps.yahoo.com.

Map of San Jose, CA. Retrieved Oct. 2, 2013 from http://maps.bing.com.

Map of San Jose, CA. Retrieved Oct. 2, 2013 from http://maps.google.com.

Microsoft—Developer Network, "Getting Started with VBA in Word 2010," Apr. 2010, <http://msdn.microsoft.com/en-us/library/ff604039%28v=office.14%29.aspx> as printed Apr. 4, 2014 in 17 pages.

Microsoft Office—Visio, "About connecting shapes," <http://office.microsoft.com/en-us/visio-help/about-connecting-shapes-HP085050369.aspx> printed Aug. 4, 2011 in 6 pages.

Microsoft Office—Visio, "Add and glue connectors with the Connector tool," <http://office.microsoft.com/en-us/visio-help/add-and-glue-connectors-with-the-connector-tool-HA010048532.aspx?CTT=1> printed Aug. 4, 2011 in 1 page.

Microsoft Windows, "Microsoft Windows Version 2002 Print Out 2," 2002, pp. 1-6.

Microsoft, "Registering an Application to a URI Scheme," <http://msdn.microsoft.com/en-us/library/aa767914.aspx>, printed Apr. 4, 2009 in 4 pages.

Microsoft, "Using the Clipboard," <http://msdn.microsoft.com/en-us/library/ms649016.aspx>, printed Jun. 8, 2009 in 20 pages.

Nadeau et al., "A Survey of Named Entity Recognition and Classification," Jan. 15, 2004, pp. 20.

Nin et al., "On the Use of Semantic Blocking Techniques for Data Cleansing and Integration," 11th International Database Engineering and Applications Symposium, 2007, pp. 9.

Nitro, "Trick: How to Capture a Screenshot as PDF, Annotate, Then Share It," <http://blog.nitropdf.com/2008/03/04/trick-how-to-capture-a-screenshot-as-pdf-annotate-it-then-share/>, Mar. 4, 2008, pp. 2.

Online Tech Tips, "Clip2Net—Share files, folders and screenshots easily," <http://www.online-tech-tips.com/free-software-downloads/share-files-folders-screenshots/>, Apr. 2, 2008, pp. 5.

O'Reilly.com, http://oreilly.com/digitalmedia/2006/01/01/mac-os-x-screenshot-secrets.html published Jan. 1, 2006 in 10 pages.

Pythagoras Communications Ltd., "Microsoft CRM Duplicate Detection," Sep. 13, 2011, https://www.youtube.com/watch?v=j-7Qis0D0Kc.

Qiang et al., "A Mutual-Information-Based Approach to Entity Reconciliation in Heterogeneous Databases," Proceedings of 2008 International Conference on Computer Science & Software Engineering, IEEE Computer Society, New York, NY, Dec. 12-14, 2008, pp. 666-669.

Schroder, Stan, "15 Ways to Create Website Screenshots," <http://mashable.com/2007/08/24/web-screenshots/>, Aug. 24, 2007, pp. 2.

Sekine et al., "Definition, Dictionaries and Tagger for Extended Named Entity Hierarchy," May 2004, pp. 1977-1980.

SnagIt, "SnagIt 8.1.0 Print Out 2," Software release date Jun. 15, 2006, pp. 1-3.

SnagIt, "SnagIt 8.1.0 Print Out," Software release date Jun. 15, 2006, pp. 6.

SnagIt, "SnagIt Online Help Guide," <http://download.techsmith.com/snagit/docs/onlinehelp/enu/snagit_help.pdf>, TechSmith Corp., Version 8.1, printed Feb. 7, 2007, pp. 284.

Warren, Christina, "TUAW Faceoff: Screenshot apps on the firing line," <http://www.tuaw.com/2008/05/05/tuaw-faceoff-screenshot-apps-on-the-firing-line/>, May 5, 2008, pp. 11.

Zhao et al., "Entity Matching Across Heterogeneous Data Sources: An Approach Based on Constrained Cascade Generalization," Data & Knowledge Engineering, vol. 66, No. 3, Sep., 2008, pp. 368-381.

International Search Report and Written Opinion in Application No. PCT/US2009/056703 dated Mar. 15, 2010.

Notice of Acceptance for Australian Patent Application No. 2013251186 dated Nov. 6, 2015.

Notice of Allowance for U.S. Appl. No. 12/556,307 dated Jan. 4, 2016.

Notice of Allowance for U.S. Appl. No. 14/222,364 dated Jul. 27, 2017.

Notice of Allowance for U.S. Appl. No. 14/265,637 dated Feb. 13, 2015.

Notice of Allowance for U.S. Appl. No. 14/304,741 dated Apr. 7, 2015.

Notice of Allowance for U.S. Appl. No. 14/805,313 dated Jun. 15, 2016.

Official Communication for Australian Patent Application No. 2013251186 dated Mar. 12, 2015.

Official Communication for Australian Patent Application No. 2014201506 dated Feb. 27, 2015.

Official Communication for Australian Patent Application No. 2014201507 dated Feb. 27, 2015.

Official Communication for Australian Patent Application No. 2014203669 dated May 29, 2015.

Official Communication for Canadian Patent Application No. 2831660 dated Jun. 9, 2015.

Official Communication for European Patent Application No. 09813700.3 dated Apr. 3, 2014.

Official Communication for European Patent Application No. 12181585.6 dated Sep. 4, 2015.

Official Communication for European Patent Application No. 14158958.0 dated Apr. 16, 2015.

Official Communication for European Patent Application No. 14158958.0 dated Jun. 3, 2014.

Official Communication for European Patent Application No. 14158977.0 dated Jun. 10, 2014.

Official Communication for European Patent Application No. 14158977.0 dated Apr. 16, 2015.

Official Communication for European Patent Application No. 15156004.2 dated Aug. 24, 2015.

Official Communication for European Patent Application No. 15179122.5 dated Sep. 11, 2015.

Official Communication for Great Britain Patent Application No. 1404573.6 dated Sep. 10, 2014.

Official Communication for Great Britain Patent Application No. 1411984.6 dated Dec. 22, 2014.

Official Communication for Netherlands Patent Application No. 2011729 dated Aug. 13, 2015.

Official Communication for Netherlands Patent Application No. 2013134 dated Apr. 20, 2015.

Official Communication for New Zealand Patent Application No. 622404 dated Mar. 20, 2014.

Official Communication for New Zealand Patent Application No. 622439 dated Mar. 24, 2014.

Official Communication for New Zealand Patent Application No. 622439 dated Jun. 6, 2014.

Official Communication for New Zealand Patent Application No. 624557 dated May 14, 2014.

Official Communication for U.S. Appl. No. 12/556,307 dated Oct. 1, 2013.

Official Communication for U.S. Appl. No. 12/556,307 dated Feb. 13, 2012.

Official Communication for U.S. Appl. No. 12/556,307 dated Mar. 14, 2014.

Official Communication for U.S. Appl. No. 12/556,307 dated Sep. 2, 2011.

Official Communication for U.S. Appl. No. 12/556,307 dated Jun. 9, 2015.

(56) References Cited

OTHER PUBLICATIONS

Official Communication for U.S. Appl. No. 12/556,321 dated Jun. 6, 2012.
Official Communication for U.S. Appl. No. 12/556,321 dated Dec. 7, 2011.
Official Communication for U.S. Appl. No. 12/556,321 dated Jul. 7, 2015.
Official Communication for U.S. Appl. No. 13/669,274 dated Aug. 26, 2015.
Official Communication for U.S. Appl. No. 13/669,274 dated May 6, 2015.
Official Communication for U.S. Appl. No. 13/831,791 dated Feb. 11, 2016.
Official Communication for U.S. Appl. No. 13/831,791 dated Mar. 4, 2015.
Official Communication for U.S. Appl. No. 13/831,791 dated Aug. 6, 2015.
Official Communication for U.S. Appl. No. 13/835,688 dated Jun. 17, 2015.
Official Communication for U.S. Appl. No. 13/835,688 dated Sep. 30, 2015.
Official Communication for U.S. Appl. No. 13/835,688 dated Jun. 7, 2016.
Official Communication for U.S. Appl. No. 13/949,043 dated Jan. 15, 2016.
Official Communication for U.S. Appl. No. 13/949,043 dated Oct. 15, 2013.
Official Communication for U.S. Appl. No. 13/949,043 dated May 7, 2015.
Official Communication for U.S. Appl. No. 14/014,313 dated Jun. 18, 2015.
Official Communication for U.S. Appl. No. 14/170,562 dated Jul. 17, 2015.
Official Communication for U.S. Appl. No. 14/170,562 dated Mar. 19, 2014.
Official Communication for U.S. Appl. No. 14/170,562 dated Oct. 2, 2015.
Official Communication for U.S. Appl. No. 14/170,562 dated Sep. 25, 2014.
Official Communication for U.S. Appl. No. 14/170,562 dated Mar. 3, 2016.
Official Communication for U.S. Appl. No. 14/222,364 dated Jun. 24, 2016.
Official Communication for U.S. Appl. No. 14/222,364 dated Dec. 9, 2015.
Official Communication for U.S. Appl. No. 14/265,637 dated Sep. 26, 2014.
Official Communication for U.S. Appl. No. 14/289,596 dated Jul. 18, 2014.
Official Communication for U.S. Appl. No. 14/289,596 dated Jan. 26, 2015.
Official Communication for U.S. Appl. No. 14/289,596 dated Apr. 30, 2015.
Official Communication for U.S. Appl. No. 14/289,596 dated May 9, 2016.
Official Communication for U.S. Appl. No. 14/289,599 dated Jul. 22, 2014.
Official Communication for U.S. Appl. No. 14/289,599 dated May 29, 2015.
Official Communication for U.S. Appl. No. 14/289,599 dated Sep. 4, 2015.
Official Communication for U.S. Appl. No. 14/304,741 dated Mar. 3, 2015.
Official Communication for U.S. Appl. No. 14/304,741 dated Aug. 6, 2014.
Official Communication for U.S. Appl. No. 14/449,083 dated Mar. 12, 2015.
Official Communication for U.S. Appl. No. 14/449,083 dated Oct. 2, 2014.
Official Communication for U.S. Appl. No. 14/449,083 dated Aug. 26, 2015.
Official Communication for U.S. Appl. No. 14/449,083 dated Apr. 8, 2016.
Official Communication for U.S. Appl. No. 14/518,757 dated Dec. 1, 2015.
Official Communication for U.S. Appl. No. 14/518,757 dated Apr. 2, 2015.
Official Communication for U.S. Appl. No. 14/518,757 dated Jul. 20, 2015.
Official Communication for U.S. Appl. No. 14/805,313 dated Dec. 30, 2015.
Official Communication for U.S. Appl. No. 14/958,855 dated May 4, 2016.
Official Communication for U.S. Appl. No. 14/975,215 dated May 19, 2016.
Official Communication for U.S. Appl. No. 14/975,215 dated Jun. 21, 2017.
Official Communication for U.S. Appl. No. 14/975,215 dated Nov. 4, 2016.
"A First Look: Predicting Market Demand for Food Retail using a Huff Analysis," TRF Policy Solutions, Jul. 2012, pp. 30.
Brandel, Mary, "Data Loss Prevention Dos and Don'ts," <http://web.archive.org/web/20080724024847/http://www.csoonline.com/article/221272/Dos_and_Don_ts_for_Data_Loss_Prevention>, Oct. 10, 2007, pp. 5.
Official Communication for U.S. Appl. No. 14/289,596 dated Aug. 5, 2015.
Official Communication for U.S. Appl. No. 14/518,757 dated Dec. 10, 2014.
Official Communication for U.S. Appl. No. 14/975,215 dated Jan. 4, 2018.
Official Communication for New Zealand Patent Application No. 622389 dated Mar. 20, 2014.
Official Communication for US Patent Application No. 14/975,215 dated Jul. 26, 2018.
Official Communication for U.S. Appl. No. 14/975,215 dated Jun. 27, 2019.

* cited by examiner

POTENTIAL PROVIDING OF UNNECESSARY PROCEDURES

Provider X
Identified by John Doe

ASSIGNED TO: Unassigned ▼

TIN: 123456 (Active)
PIN: 9876
NPI: 456789
Total Exposure: $24,520

State: CA
Phone: 415-555-5555
Participation: Non-par
Specialization: Pediatrics

| CPT Code | Unique Claims | Billed | Paid |
|---|---|---|---|
| 99214 | 234 | $21,349 | $12,445 |
| 99356 | 1092 | $104,287 | $87,561 |
| 99203 | 24 | $4,310 | $2,980 |
| 99355 | 37 | $7,122 | $5,333 |
| 99215 | 8 | $240 | $180 |
| Total | | | $108,499 |

NOTES

Provider X was identified for providing unnecessary procedures from January 1, 2011 to March 31, 2015 because 75% of members were billed for Procedure 1, 80% of members were billed for Procedure 2, and 94% of members were billed for Procedure 3. Typical providers that offer Procedure 1, Procedure 2, or Procedure 3 generally have 23% of members being billed for Procedure 1, 12% of members being billed for Procedure 2, and 30% of members being billed for Procedure 3.

Additional Notes

Code Distribution | Known Locations | Paid to TIN

MAP

FIG. 5

FRAUD LEAD DETECTION SYSTEM FOR EFFICIENTLY PROCESSING DATABASE-STORED DATA AND AUTOMATICALLY GENERATING NATURAL LANGUAGE EXPLANATORY INFORMATION OF SYSTEM RESULTS FOR DISPLAY IN INTERACTIVE USER INTERFACES

CROSS-REFERENCE TO RELATED APPLICATIONS

This application claims priority under 35 U.S.C. § 119(e) to U.S. Provisional Application No. 62/180,495, entitled "MEDICAL CLAIMS FRAUD LEAD DETECTION AND PRESENTATION" and filed on Jun. 16, 2015, and U.S. Provisional Application No. 62/211,327, entitled "MEDICAL CLAIMS FRAUD LEAD DETECTION SYSTEM FOR EFFICIENTLY PROCESSING DATABASE-STORED DATA AND AUTOMATICALLY GENERATING NATURAL LANGUAGE EXPLANATORY INFORMATION OF SYSTEM RESULTS FOR DISPLAY IN INTERACTIVE USER INTERFACES" and filed on Aug. 28, 2015, which are hereby incorporated by reference in their entireties.

TECHNICAL FIELD

The present invention relates to processing database-stored data and automatically generating natural language explanatory information of system results.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

A database and/or a system of databases may store a large quantity of data. For example, a database or a system of databases can receive and store data related to a large number of health care claims (e.g., medical procedure claims, medical equipment claims, prescription claims, doctor office claims, etc.) that are submitted over a period of time. The health care claims data can be supplemented with other data, such as user contact information, medical code information, and/or the like, and the supplemental data can also be stored in the database and/or the system of databases.

In some cases, a user may attempt to analyze a portion of the stored data. For example, the user may attempt to analyze a portion of the stored data to identify leads to potential health care misuse. However, as the number of measurements increases over time, it can become very difficult for the user to identify the relevant data and perform the analysis.

SUMMARY

Techniques are described herein for automatically processing data stored in one or more databases using machine learning to detect entities (such as health care providers, health care plan members, patients, pharmacies, and so forth) associated with health care claims that are suspected of fraudulent, wasteful, and/or abusive activity. The techniques may further or alternatively involve generating and presenting, for a set of suspected entities, natural language explanatory information explaining how and/or why each of the respective suspected entities is considered to be suspected of fraudulent, wasteful, and/or abusive activity. Feedback provided by fraud analysts and/or other subject matter experts in the misuse detection space is used to facilitate misuse detection and misuse detection presentation.

One aspect of the disclosure provides a method for processing a large amount of dynamically updating data. The method comprises automatically detecting an instance of suspected misuse by an entity associated with a claim; in response to automatically detecting, calculating a degree of similarity between the detected instance and each of one or more known instances of misuse, each of the known instances corresponding to a known entity associated with one or more respective claims; automatically identifying one or more similar known instances of misuse from among the one or more known instances of misuse based on the degree of similarity calculated between the detected instance and each of the one or more known instances of misuse; generating explanatory information for the detected instance, the explanatory information including an indication of similarity of the detected instance to the one or more similar known instances of misuse; and causing the explanatory information to be automatically presented with the detected instance during presentation of information about the detected instance, where the method is performed using one or more processors.

The method of the preceding paragraph can have any sub-combination of the following features: where calculating the degree of similarity comprises calculating a weighted distance between the detected instance and each of the one or more known instances of misuse; where calculating the degree of similarity comprises calculating the degree of similarity using a k-nearest neighbor (KNN) technique; where automatically detecting the instance comprises automatically detecting the instance using a misuse detection model; where the method further comprises prior to automatically detecting the instance, automatically detecting the one or more known instances of misuse as being suspected of misuse using the misuse detection model, and receiving, from an independent source, a confirmation of misuse of the one or more known instances of misuse, where the one or more known instances of misuse are available for calculating the degree of similarity after receiving the confirmation; where the method further comprises receiving, from the independent source, the confirmation of misuse for the detected instance, wherein the detected instance becomes a known instance of misuse for a next one of a detected instance; where the independent source comprises one or more claim misuse analysts; where the method further comprises performing machine learning to generate the misuse detection model; where the misuse detection model is an outlier detection model, and wherein automatically detecting an instance of suspected misuse by an entity associated with a claim further comprises determining, for the entity, types of procedures performed by the entity, determining, for each type of procedure, a first percentage of members that receive services from the entity that receive the respective procedure, analyzing, for each type of procedure performed by the entity, the first percentage and second percentages of members that receive the respective procedure determined for other entities to determine a threshold value, and determining that the first percentage is less than the threshold value; and where the entity is one of a health care provider, a health care member, a patient, or a pharmacy.

Another aspect of the disclosure provides one or more non-transitory machine-readable media storing instructions which, when executed by one or more processors, cause automatically detecting an instance of suspected misuse by an entity associated with a claim; in response to automatically detecting, calculating a degree of similarity between the detected instance and each of one or more known instances of misuse, each of the known instances corresponding to a known entity associated with one or more respective claims; automatically identifying one or more similar known instances of misuse from among the one or more known instances of misuse based on the degree of similarity calculated between the detected instance and each of the one or more known instances of misuse; generating explanatory information for the detected instance, the explanatory information including an indication of similarity of the detected instance to the one or more similar known instances of misuse; and causing the explanatory information to be automatically presented with the detected instance during presentation of information about the detected instance.

The one or more non-transitory machine-readable media of the preceding paragraph can have any sub-combination of the following features: where calculating the degree of similarity comprises calculating the degree of similarity using a k-nearest neighbor (KNN) technique; where automatically detecting the instance comprises automatically detecting the instance using a misuse detection model; where the instructions, when executed by the one or more processors, further cause: prior to automatically detecting the instance, automatically detecting the one or more known instances of misuse as being suspected of misuse using the misuse detection model, and receiving, from an independent source, a confirmation of misuse of the one or more known instances of misuse, where the one or more known instances of misuse are available for calculating the degree of similarity after receiving the confirmation; and where the entity comprises a health care provider, a health care member, a patient, or a pharmacy.

Another aspect of the disclosure provides a system configured to process a large amount of dynamically updating data. The system comprises one or more databases including a plurality of claims data; a detection component, at least partially implemented by computing hardware, configured to automatically detect an instance of suspected misuse by an entity associated with a claims data from among the plurality of claims data; a similarity component, at least partially implemented by computing hardware, configured to identify one or more known instances of misuse similar to the detected instance, each of the known instances corresponding to a known entity associated with a respective claims data from among the plurality of claims data; and a generation component, at least partially implemented by computing hardware, configured to generate misuse explaining information for the detected instance, the misuse explaining information including an indication of similarity of the detected instance to each of the one or more known instances of misuse identified by the similarity component, and appending the misuse explaining information to the detected instance for presentment.

The system of the preceding paragraph can have any sub-combination of the following features: where the similarity component identifies the one or more known instances of misuse similar to the detected instance based on calculation of a weighted distance between the detected instance and each of the one or more known instances of misuse; where the detection component uses a misuse detection model to automatically detect the instance, the misuse detection model is a function of a combination of weighted features of at least one misuse; where the detection component automatically detects, prior to automatic detection of the instance, the one or more known instances of misuse as being suspected of misuse using the misuse detection model, and further comprising a user interface component, at least partially implemented by computing hardware, configured to receive from an independent source, a confirmation of misuse of the one or more known instances of misuse, where the one or more known instances of misuse are available for identification by the similarity component after the user interface component receives the confirmation; and where the system further comprises a user interface component, at least partially implemented by computing hardware, configured to receive from an independent source, a confirmation of misuse for the detected instance, wherein the detected instance becomes a known instance of misuse for a next one of a detected instance.

Additional embodiments of the disclosure are described below in reference to the appended claims, which may serve as an additional summary of the disclosure.

In various embodiments, computer systems are disclosed that comprise one or more hardware computer processors in communication with one or more non-transitory computer readable storage devices, wherein the one or more hardware computer processors are configured to execute the plurality of computer executable instructions in order to cause the computer system to operations comprising one or more aspects of the above-described embodiments (including one or more aspects of the appended claims).

In various embodiments, computer-implemented methods are disclosed in which, under control of one or more hardware computing devices configured with specific computer executable instructions, one or more aspects of the above-described embodiments (including one or more aspects of the appended claims) are implemented and/or performed.

In various embodiments, non-transitory computer-readable storage mediums storing software instructions are disclosed, wherein, in response to execution by a computing system having one or more hardware processors, the software instructions configure the computing system to perform operations comprising one or more aspects of the above-described embodiments (including one or more aspects of the appended claims).

Further, as described herein, various embodiments of the system may be configured and/or designed to generate user interface data useable for rendering the various interactive user interfaces described. The user interface data may be used by the system, and/or another computer system, device, and/or software program (for example, a browser program), to render the interactive user interfaces. The interactive user interfaces may be displayed on, for example, electronic displays (including, for example, touch-enabled displays).

BRIEF DESCRIPTION OF THE DRAWINGS

FIG. 5 illustrates a user interface illustrating an example lead summary report for a particular identified lead.

DETAILED DESCRIPTION

Figure 1:
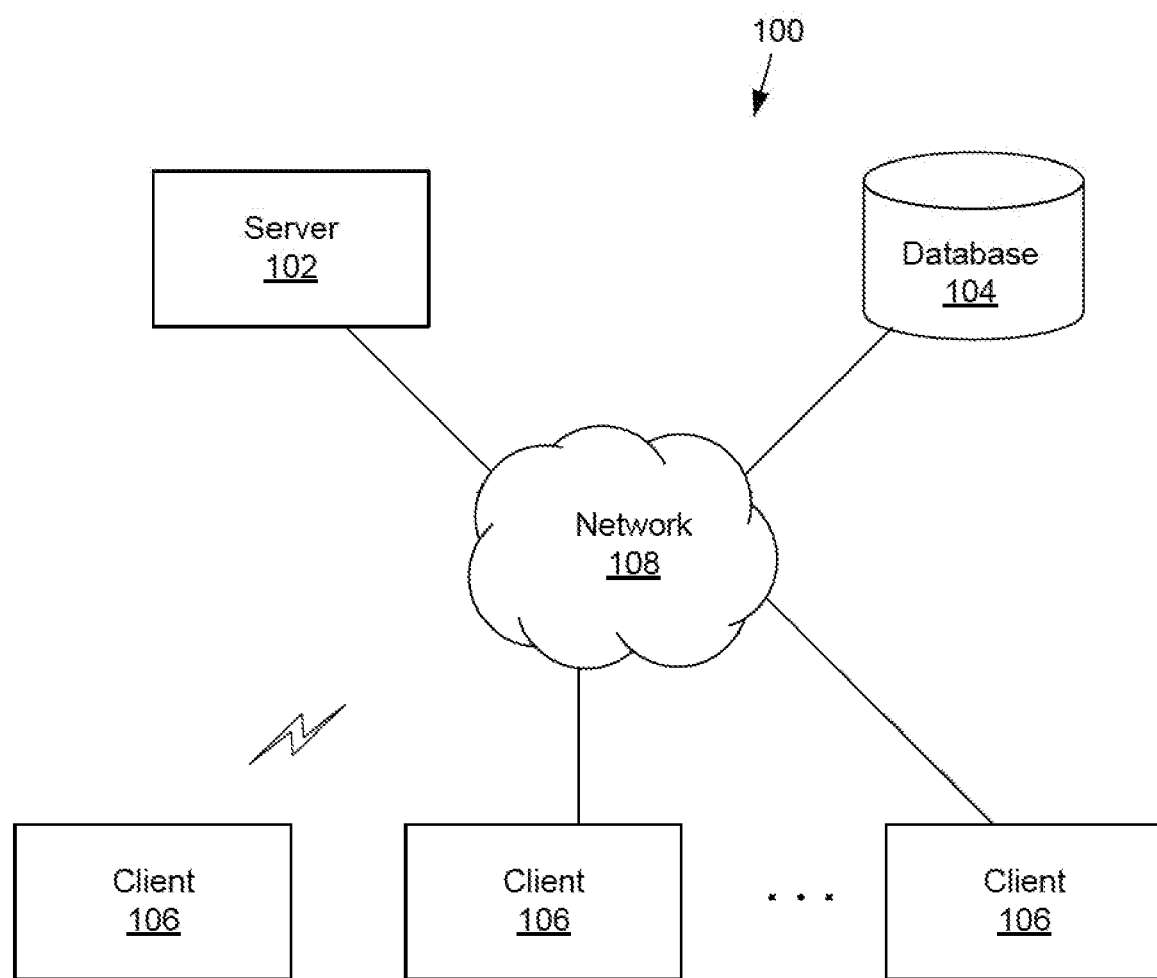
FIG. 1 illustrates an example system for automatically composing complex database queries according to some embodiments.

In the following description, for the purposes of explanation, numerous specific details are set forth in order to provide a thorough understanding of the present disclosure. It will be apparent, however, that the present disclosure may be practiced without these specific details. In other instances, well-known structures and devices are shown in block diagram form in order to avoid unnecessarily obscuring the present disclosure.

While the disclosure is described herein with respect to fraud and fraud lead detection, this is merely for illustrative purposes and is not meant to be limiting. For example, the techniques described herein can apply to waste lead detection and/or abuse lead detection. Health care waste, fraud and/or abuse may be examples of health care misuse. As used herein, fraud refers to knowingly and willfully executing, or attempting to execute, a scheme or artifice to defraud any health care program or entity or to obtain any of the money or property owned by, or under the custody or control of, any health care program or entity. Waste refers to the overutilization of services or other practices that, directly or indirectly, result in unnecessary costs to the health care system. Abuse refers to any action that may, directly or indirectly, result in one or more of unnecessary costs to the health care system, improper payment for services, payment for services that fail to meet professionally recognized standards of care, and/or services that are medically unnecessary.

1.0 General Overview

Prescription claims, doctor office claims, medical procedure claims, hospital claims, medical equipment claims, and other medical claims (collectively referred to as medical claims or healthcare claims) may number in the millions or billions per year. And each medical claim may include numerous types of data, such as billing codes (e.g., procedure code, diagnosis code, etc.), patient identifier, location, service provider identifier, service date, and the like. Thus, while databases of medical claims contain vast amount of information, selectively mining the available information for useful purposes, such as to identify leads to potential fraudulent claims, is not a trivial task. Moreover, even the selectively mined information may comprise a large number of identified leads (e.g., numbering in the thousands or tens of thousands), which may be daunting for fraud analysts to assess and select for further action.

Accordingly, techniques are described herein for automatically detecting entities (such as health care providers, health care plan members, patients, pharmacies, and so forth) associated with health care claims that are suspected of fraudulent activity. The techniques may further or alternatively involve presenting a set of suspected entities with information explaining how and/or why each of the respective suspected entities is considered to be suspected of fraudulent activity. Feedback provided by fraud analysts and/or other subject matter experts in the fraud detection space is used to facilitate fraud detection and fraud detection presentation.

In an embodiment, a programmatic method enables machine learning to improve one or more fraud detection models over time. One or more fraud detection models are iteratively trained using known outcomes of analyses of previously suspected entities. The known outcomes may include, for example, a fraud analysts' conclusion as to whether one or more of the previously suspected entities were actually involved in fraud, a fraud analysts' decision as to whether to escalate one or more of the previously suspected entities for more detailed investigation (e.g., by specialized investigators), and/or the like. In addition, one or more fraud detection models can be trained using unsupervised techniques (e.g., outlier detection). In an embodiment, a programmatic method enables generation of one or more fraud detection models based on metrics or features of fraud learned from other fraud detection model(s) and/or provided by insights from fraud analysts and/or other subject matter experts in the fraud detection space.

In an embodiment, a natural language explanation accompanying a report of one or more suspected entities is configured to impart familiarity to fraud analysts reviewing a set of suspected entities. The explanation relates a given current suspected entity with one or more previously suspected entities determined by fraud analysts to have been involved in fraudulent activit(ies). The explanation may also or instead relate a given current suspected entity to one or more fraud detection models trusted by fraud analysts, one or more fraud detection theories trusted by fraud analysts, and so forth.

Among other aspects, the described systems and techniques permit leveraging of domain- and experience-based knowledge in fraud detection and fraud detection presentation. The systems and techniques further permit, among other aspects, improved fraud detection through iterative machine learning. Among yet other aspects, the systems and techniques further improve efficiency and accuracy of fraud analysts' workflow, because some or all of the currently suspected entities identified by the automated fraud detection techniques are automatically given context in relation to previous points of reference known, trusted, and/or used by fraud analysts.

2.0 Structural Overview

Various modifications to the embodiments will be readily apparent to those skilled in the art, and principles defined herein may be applied to other embodiments and applications without departing from the spirit and scope of the invention. Moreover, in the following description, numerous details are set forth for the purpose of explanation. However, one of ordinary skill in the art will realize that embodiments of the invention may be practiced without the use of these specific details. In other instances, well-known structures and processes are not shown in block diagram form in order not to obscure the description of the invention with unnecessary detail. Thus, the present disclosure is not intended to be limited to the embodiments shown, but is to be accorded the widest scope consistent with the principles and features disclosed herein.

FIG. 1 illustrates an example system 100 in which the techniques described may be practiced, according to some embodiments. System 100 is a computer-based system. The various components of system 100 are implemented at least partially by hardware at one or more computing devices, such as one or more hardware processors executing instructions stored in one or more memories for performing various functions described herein. System 100 illustrates only one of many possible arrangements of components configured to perform the functionality described herein. Other arrangements may include fewer or different components, and the division of work between the components may vary depending on the arrangement.

System 100 includes a server 102, a database 104, one or more clients 106, and a network 108. Each of the server 102, database 104, and clients 106 is in wired or wireless communication with the network 108.

Server 102 comprises one or more servers, computers, processors, database servers, and/or computing devices configured to communicate with the database 104 and/or clients 106 via network 108. The server 102 facilitates performance of the techniques described herein. Server 102 hosts one or more applications, websites, or other visual or user interface mechanisms related to use of medical claims data as described in detail below. Server 102 may be located at one or more geographically distributed locations. Although one server 102 is shown in FIG. 1, system 100 may, depending on the embodiment, comprise one, two, or any number of servers 102, which may work alone and/or collectively to provide the functionality described herein.

Database 104 comprises one or more databases or storage devices configured to store and maintain medical claims data, data associated with medical claims data, data associated with fraud detection or fraud detection lead generation, data associated with fraud lead explanation, and/or instructions for use by server 102 and/or clients 106 as described herein. In other embodiments, the database 104 also stores and maintains pharmacy claims data and/or data associated with pharmacy claims data. Pharmacy claims data may be used in a similar manner as how medical claims data is used and described herein. Database 104 may, in some embodiments, be located at one or more geographically distributed location relative to server 102. Server 102 and/or clients 106 may, in some embodiments, access database 104 via network 108. Alternatively, server 102 may access database 104 without needing network 108. As another alternative, database 104 may be included within server 102. System 100 may, depending on the embodiment, comprise one, two, or any number of databases 104 configured to individually and/or collectively store the data described herein.

Clients 106 comprise computing devices, including but not limited to, work stations, personal computers, general purpose computers, laptops, Internet appliances, hand-held devices, wireless devices, wired devices, portable devices, wearable computers, cellular or mobile phones, portable digital assistants (PDAs), smart phones, tablets, multi-processor systems, microprocessor-based or programmable consumer electronics, game consoles, set-top boxes, network PCs, mini-computers, and the like. Each of the clients 106 includes applications, software, and/or other executable instructions to facilitate various aspects of the medical claim fraud detection techniques described herein. Clients 106 may also include additional applications or other interface capabilities to communicate with the server 102 and/or database 104. Clients 106 may, depending on the embodiment, be located geographically dispersed from each other. Although three clients 106 are shown in FIG. 1, more or less than three clients 106 may be included in system 100. Clients 106 are also referred to as devices, requesting devices, requesting clients, requesting machines, requestors, and the like.

Network 108 comprises a communications network, such as a local area network (LAN), a wireless LAN (WLAN), a wide area network (WAN), a wireless WAN (WWAN), a metropolitan area network (MAN), an ad hoc network, an intranet, an extranet, a virtual private network (VPN), a portion of the Internet, the Internet, a portion of a public switched telephone network (PSTN), a cellular network, or a combination of two or more such networks. When network 108 comprises a public network, security features (e.g., VPN/SSL secure transport) may be included to ensure authorized access within system 100.

Figure 2:
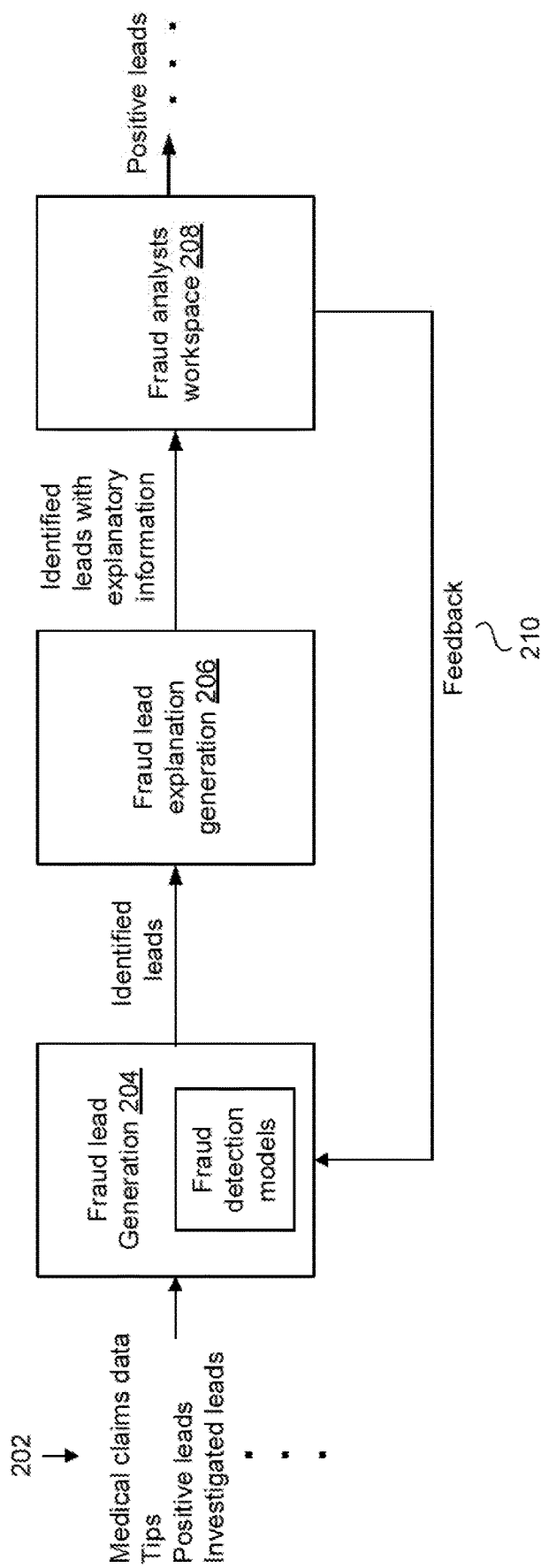
FIG. 2 illustrates an example portion of a fraud detection framework of the system of FIG. 1 according to some embodiments.

FIG. 2 illustrates components of a computer-based system forming an example portion of a fraud detection framework, according to an embodiment. A plurality of data 202 including, but not limited to, medical claims data, pharmacy claims data, fraud tips (e.g., from news publications, blogs, consumer or provider reports, criminal investigations, etc.), previous positive leads, previous investigated leads, example positive leads, and the like are fed into a fraud lead generation module 204. The fraud lead generation module 204 includes one or more fraud detection models, also referred to as models, that are used to identify one or more fraud leads from among the medical claims data. Each of the fraud leads comprises identification of a potential fraud-related entity, such as a medical service or product provider, pharmacist, or health care plan member (e.g., patient), or a medical claim that involves such an entity or group of entities. The identification of fraud leads may also include ranking the leads from most to least suspected of fraudulent activity.

A fraud lead explanation generation module 206 generates graphical and/or textual information to accompany each of the identified fraud leads. The graphical and/or textual information provides a natural language explanation or context for the respective fraud lead, such as explaining how the lead is similar to a previous lead deemed to be a positive lead, or explaining the reasoning behind how the lead was identified (e.g., explaining the fraud detection model used to identify the lead in readily understandable and relatable terms). The graphical and/or textual information appended to each of the respective fraud leads is generated with fraud analysts in mind.

The fraud leads and accompanying explanation are provided to one or more fraud analyst workspaces 208 for review and further action. The fraud analysts assess the fraud leads and explanations to determine, at a minimum, which of the fraud leads appear to be related to fraudulent activity (e.g., positive leads) and label or flag such fraud leads accordingly. At least some of the positive leads may then be actionable as investigative leads. In turn, some of the positive investigative leads may result in notifying insurers or law enforcement personnel. In addition, fraud analysts may also label, flag, annotate, or otherwise indicate fraud leads that do not appear to be related to fraudulent activity (e.g., negative leads), explain why a lead is deemed to be negative lead, provide intuitive- or domain-based knowledge relating to fraud detection that is not necessarily associated with the provided fraud leads, and/or other information.

Information provided by fraud analysts may collectively be referred to as feedback 210. Feedback 210 may be captured by machines via interactions on fraud analyst workspaces 208 and/or humans via manual interviews and the like. Feedback 210 from fraud analysts is an input into the fraud lead generation module 204. Fraud lead generation module 204, in turn, uses at least a portion of the feedback 210 to refine existing fraud detection models and/or to identify new fraud detection models. In some embodiments, fraud analysts' inputs and feedback enable implementation of machine learning techniques in connection with fraud detection models included in the fraud lead generation module 204.

Although not shown, feedback may also be provided to fraud lead generation module 204 from downstream-related activities associated with the leads. For example, investigative-related outcomes of one or more leads identified by module 204 would be relevant to assess the fidelity of fraud detection models used to identify those leads. Information such as which leads were selected for further investigation, or the investigative outcome of leads, may be returned to module 204 via various data importation and/or input solicitation processes. Incorporation of assessment of previous outputs (e.g., identified leads) as current inputs to the fraud lead generation module 204 forms a virtuous circle to improve the fraud detection framework.

Figure 3:
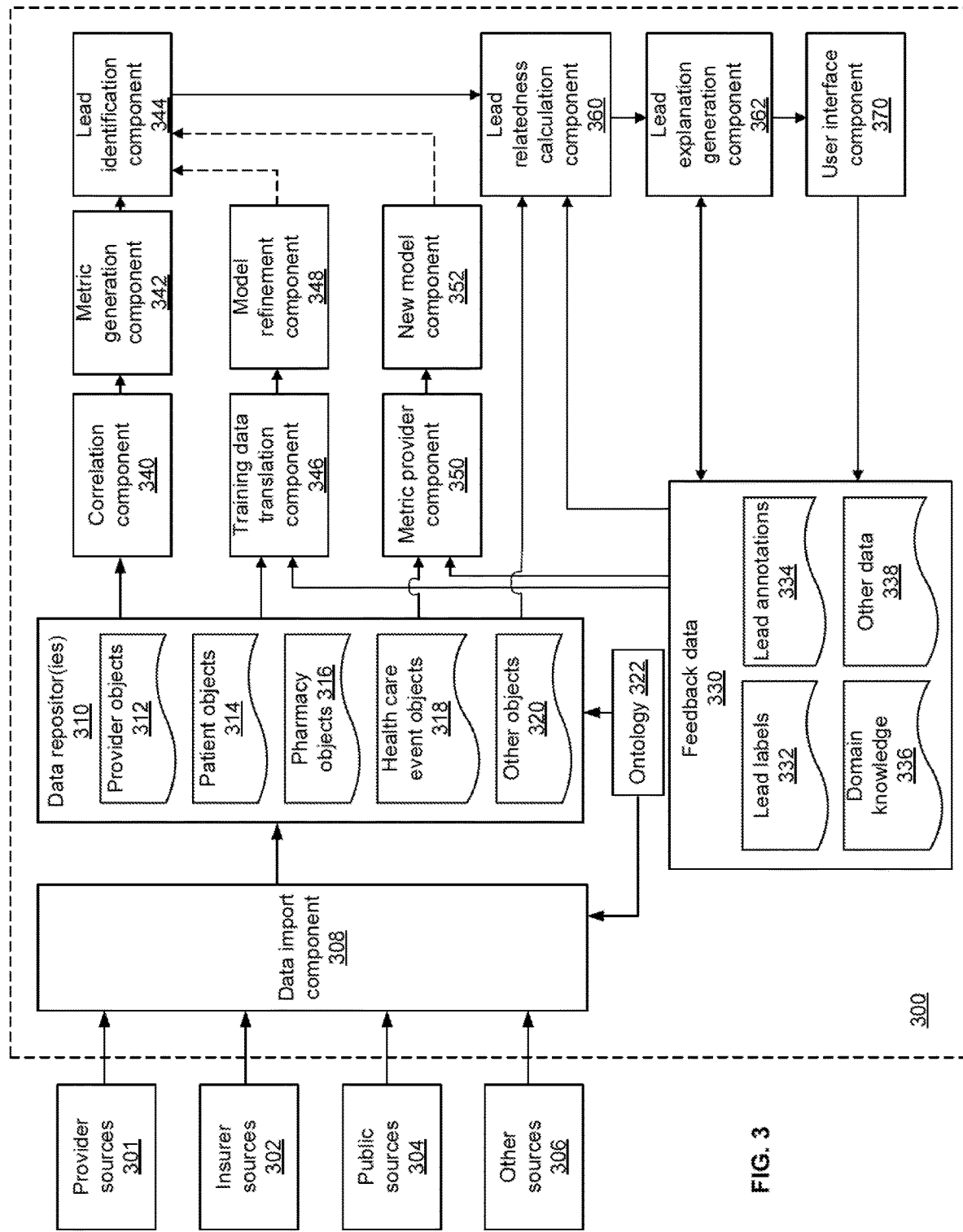
FIG. 3 illustrates example additional details of the system of FIG. 1 according to some embodiments.

FIG. 3 illustrates a system 300 comprising various example objects and components that may be utilized to perform fraud lead generation and fraud lead explanation generation, according to some embodiments. System 300 is a computer-based system. The various components of system 300 are implemented at least partially by hardware at one or more computing devices, such as one or more hardware processors executing instructions stored in one or more memories for performing various functions described herein. The components are communicatively coupled (e.g., via appropriate interfaces) to each other and to various data sources, so as to allow information to be passed between the components and/or to share and access common data. System 300 illustrates only one of many possible arrangements of components configured to perform the functionality described herein. Other arrangements may include fewer or different components, and the division of work between the components may vary depending on the arrangement. In an embodiment, system 300 is implemented by one or more of the computer systems 100 and/or 600 described herein.

System 300 comprises a data import component 308 which collects data from a variety of sources, including one or more of provider sources 301, insurer sources 302, public sources 304, and/or other sources 306 as described herein. The data may be collected from each included source 301-306 on one or on multiple occasions, depending on factors such as the size of the data source, the accessibility of the data source, and how frequently the data source changes. Depending on the form in which the data is collected, the data import component 308 may optionally perform Extract, Transform, and Load ("ETL") operations on the collected data to generate objects that conform to one or more defined ontologies 322. Ontologies 322 may be, for example, dynamic ontologies, static schemas, and/or other data structure definitions.

The data import component 308 causes the collected data to be stored in one or more repositories of data 310. The one or more repositories of data 310 may store, among other object types, some or all of: provider objects 312, patient objects 314, pharmacy objects 316, health care event objects 318, and/or other objects 320, each of which corresponds to a different discrete object type defined by the one or more ontologies 322. Other objects 320 may include any category of object type deemed desirable. For example, another object type may be administrative event objects. Thus, in an embodiment, data obtained from healthcare providers, insurers, public sources, and other sources may be represented in computer storage using object-oriented data representation techniques to represent providers, patients, pharmacies, events, and other items as objects that may be selectively queried to identify real-world relationships, events, or transactions suspected of fraud. Repositories 310 may be included in, for example, the database(s) 104. Repositories 310 may be collectively referred to as a medical claims repository. Examples of repositories 310 and corresponding objects 312-320 are described in subsequent sections. In some embodiments, some or all of the contents of repositories 310 may be organized as relational data instead of or in addition to object-oriented representations.

System 300 also includes one or more of feedback data 330. The one or more feedback data 330 may store, among other object types, lead labels 332, lead annotations 334, domain knowledge 336, and/or other data 338, each of which may be utilized for developing fraud detection models and/or presenting identified leads to users (e.g., fraud analysts) of system 300. Lead labels 332 are labels, flags, or other fraud-related categorizing indicators (e.g., "no fraud," "yes fraud," "fraud indeterminate," "prioritize for investigation," etc.) associated with respective fraud leads identified by the fraud detection module 204. A lead label 332 may be generated in response to input from a user in a computer interface configured to assist the user in review, assessment, or investigation of an identified lead (e.g. suspected entity or claim), or responsive to receiving data indicating other downstream activity taken in relation to the lead. Lead annotations 334 comprise notes, explanations, supplemental information, musings, impressions, items for further action, reasons for labelling a lead a particular way, or other annotations associated with respective identified fraud leads, and may be generated in manners similar to lead labels 332. Not all of the identified fraud leads may have an associated lead label 332 and/or lead annotation 334. For example, fraud analysts may label leads deemed to be positive leads, but not label leads having other dispositions. Similarly, some or all of the positive leads may have an associated annotation, while leads with certain other dispositions may have no associated annotations.

Domain knowledge 336 comprises experience- and/or intuitive-based heuristics from fraud analysts or experts about how they detect medical claims fraud. The heuristics may comprise rules or shortcuts to explain how certain decisions were made, how certain judgments were made, and the like. For example, fraud analysts may have insights into features, metrics, or properties of fraudulent entities (e.g., providers, patients, pharmacy) that are not reflected by fraud detection models to date. As another example, fraud analysts may have insights into features, metrics, or properties of fraudulent entities that are improperly expressed in the fraud detection models to date. As still another example, fraud analysts may know to look for specific items to validate or invalidate suspected fraud that machine detectors and/or persons configuring the machine detectors are unaware of. To this and other ends, the analysts may configure various business rules based upon features, metrics, and/or properties derived from objects 312-320. These business rules may be applied to leads identified by fraud models to filter, add, prioritize, and/or reprioritize leads after they have been identified by the fraud models, but prior to presentation to users.

Other data 338 comprises all other possible information pertaining to the identified fraud leads and/or for improving fraud detection. For example, other data 338 may comprise downstream data from a fraud detection workflow, such as investigative outcome of a subset of identified leads escalated for investigation, including the amount of money exposed and/or recovered. As another example, tips provided by persons or noticed from a news article may comprise other data 338. Some of the feedback data 330 may be machine-captured as part of the fraud detection workflow (e.g., lead labels 332), while other of the feedback data 330 may be manually captured using interviews or question/answer sessions (e.g., domain knowledge 336).

System 300 also comprises a correlation component 340 that correlates objects 312-320, in accordance with the techniques set forth herein. A metric generation component 342 calculates various metrics based on objects 312-320 and/or other data. Correlations produced by correlation component 340 may further be used to generate some of these metrics. Example metrics are described in other sections. Certain relationships and/or correlations of objects may suggest fraudulent activity. In an embodiment, a lead identification component 344 (also referred to as a lead detection component) identifies "leads" for suspected fraudulent activity, in accordance with the techniques described subsequently. The leads may be, for example, particular objects within repositories 310, or relationships of multiple objects. At least some of the leads may be identified based on metrics values calculated by metric generation component 342 and deemed to be suspected fraudulent entities based on various fraud detection or pattern recognition processes.

The fraud detection or pattern recognition techniques (collectively referred to as fraud detection models or models) used by the lead identification component 344 may optionally be provided by model refinement component 348 and/or new model component 352. To be discussed in detail below, at least the model refinement component 348 implements machine learning techniques to refine or improve existing fraud detection model(s). The refinement is an iterative process using on one or more sets of training data that are translated or converted into useable format by a training data translation component 346. The new model component 352 identifies new fraud detection model(s), which may use modeling techniques not implemented by the existing fraud detection models and/or data from a metric provider component 350.

A lead-relatedness calculation component 360 (also referred to as a lead-similarity component) determines how some or all of the identified leads provided by the lead identification component 344 relates to certain previous leads. For instance, the lead-relatedness calculation component 360 may determine that an identified lead is, based on various calculations and/or functions, similar in characteristics to, or identified for similar reasons as, one or more previous leads that were determined to actually correspond to fraudulent activity, or one or more previous leads that led to follow-up investigations. The lead-relatedness calculation component 360 may also or instead identify a type of accompanying explanation (e.g., a natural language explanation) or presentation material suitable for reporting the respective identified lead. Such accompanying explanation or presentation material provides a starting point, context, and user-friendly reasoning as to how the respective identified lead was found by system 100 to be a suspected fraudulent entity.

A lead explanation generation component 362 generates the appropriate explanation or presentation material to append to each of the respective identified leads. A user interface component 370 facilitates presentation of each of the identified leads and associated explanation to one or more fraud analysts at one or more of clients 106. The user interface component 370 also facilitates receiving inputs from fraud analysts interfacing at clients 106, inputs such as labeling of the identified leads or annotations associated with the identified leads; which in turn may be stored in the repository for feedback data 330.

In one embodiment, components 340-370 comprise one or more software components, programs, applications, or other units of code base or instructions configured to be executed by one or more processors included in a server 102 of system 100. In other embodiments, the functionalities or operations of one or more of components 340-370 is handled by one or more clients 106, or shared between one or more servers 102 and one or more clients 106. As an example, the functionalities of the user interface component 370 may be provided by a client 106, while those of components 340-362 are provided by a server 102. Although components 340-370 are depicted as distinct components in FIG. 3, components 340-370 may be implemented as fewer or more components than illustrated. Any of components 340-370 may communicate directly or over a network with one or more devices included in the system 100, such as server 102, database 104, or clients 106, as needed to implement the functionality described herein.

3.0 Functional Overview

Techniques are described herein for modeling data related to health care and using the models in combination with detection processes to identify fraud. In general, the techniques described herein utilize data obtained or extracted from various sources of health care data. The data are then transformed into various stored data objects, relationships and graphs that conform to one or more models for health care data, such as a dynamic ontology or schema. The data types defined by the models provide for at least: one or more data objects describing patients and/or health care plan members, one or more data objects describing health care providers, and/or individual doctors, and one or more data objects describing health care events such as prescriptions, claims, treatments, and/or procedures. In embodiments, other data objects describing a variety of other health care entities, places, and events also exist. Various examples are described herein.

3.1 Fraud Investigations

In an embodiment, the data objects and components depicted in FIG. 3 are used at various points of a workflow for identifying misuse (e.g., fraud, waste, and/or abuse). The first stage is lead generation. This stage involves identifying suspected cases of health care fraud for further investigation. A lead, as described herein, is a particular individual, organization, or event that is suspected as consisting of, relating to, or indicating actual or possible fraud, or is at an increased probability for consisting of, relating to, or indicating fraud. The term lead may also be used herein to refer to a data object that represents the suspicious individual, organization, or event. One way to identify leads is to receive tips concerning potentially fraudulent activities. Another way to identify leads is to review networks of individuals and/or organizations connected to instances of fraud described in media reports, indictments, or other publications. Another way to identify leads is to apply business rules to the various data objects and relationships described herein to flag potentially fraudulent activity, such as a male receiving treatment for ovarian cancer. Another way to identify leads is to deploy computer-implemented algorithms and/or analytical processes that calculate metrics based on the various data objects described herein, such as a metric that indicates the number of prescriptions written by each doctor for commonly abused drugs. Data objects associated with unusual values for these metrics may be investigated as leads. In embodiments described herein, leads are identified automatically using one or more fraud detection models comprising various functions in which a variety of factors, including those described above, may be quantified and weighted according to feedback from previously identified leads.

The next stage is lead prioritization. There may be many possible leads to investigate, but limited resources to investigate such leads; lead prioritization enables focusing limited resources on the leads that are given higher priority. Lead prioritization may comprise, for instance, filtering the set of leads based on one or more of: which leads involve certain types of fraud, which leads involve at least a certain threshold amount of money, which leads constitute the most obvious cases of fraud, which leads are easiest to investigate, or which leads are closely clustered. In an embodiment, various metrics that consider these and/or other factors may be used to rank the leads, and the leads may then be investigated in order of rank. In an embodiment, two primary metrics for ranking leads are configured to quantify likeliness of fraud, and impact of fraud if fraud has in fact occurred. However, a variety of other metrics for ranking leads may be created. Different investigators may be responsible for investigating leads prioritized based on different factors or metrics. In an embodiment, leads may be ranked by functions that are specific to the fraud detection model by which they were identified, and/or by functions that consider the leads independently of the fraud detection model(s) by which they were identified.

The next stage is investigation of a prioritized lead. During this stage, an investigator may seek answers to questions such as, to whom are the implicated doctors prescribing, who picks up the prescriptions involved, what medical treatments are the doctors performing, are any of those medical treatments suspect, with what larger network of other providers do the suspects interact, are any of the other providers suspect, do the providers refer other people who then prescribe drugs that are not supposed to be prescribed based on the facts involved, and so forth. In an embodiment, various data visualization and interfacing techniques for depicting the data objects described herein simplify this investigation. For example, networks of doctors, patients, and pharmacies may be depicted as navigable graphs of interconnected nodes, in which the connections are determined based on various health care events.

The fourth stage is to take action upon a positive investigation of a lead. For some patients, for example, this may involve making an intervention such as providing treatment for addiction or depression. For other patients, and for fraudulent providers, the action may involve turning over findings to an insurer and/or to law enforcement, or requesting additional information from the provider, such as patient medical records. In an embodiment, this phase may further involve generating and storing one or more data records indicating the disposition of an investigation (e.g., as positive or negative), and optionally storing annotations such as described herein, in response to user input processes and/or other suitable processes. These data records may then be utilized to derive feedback for the fraud detection model(s).

The above workflow is provided as an example. Other workflows for investigations of fraud may include different elements in varying arrangements. The data objects described herein are likewise useful in these other workflows.

3.2 Automated Identification of Leads and Associated Explanation Information

Figure 4A:
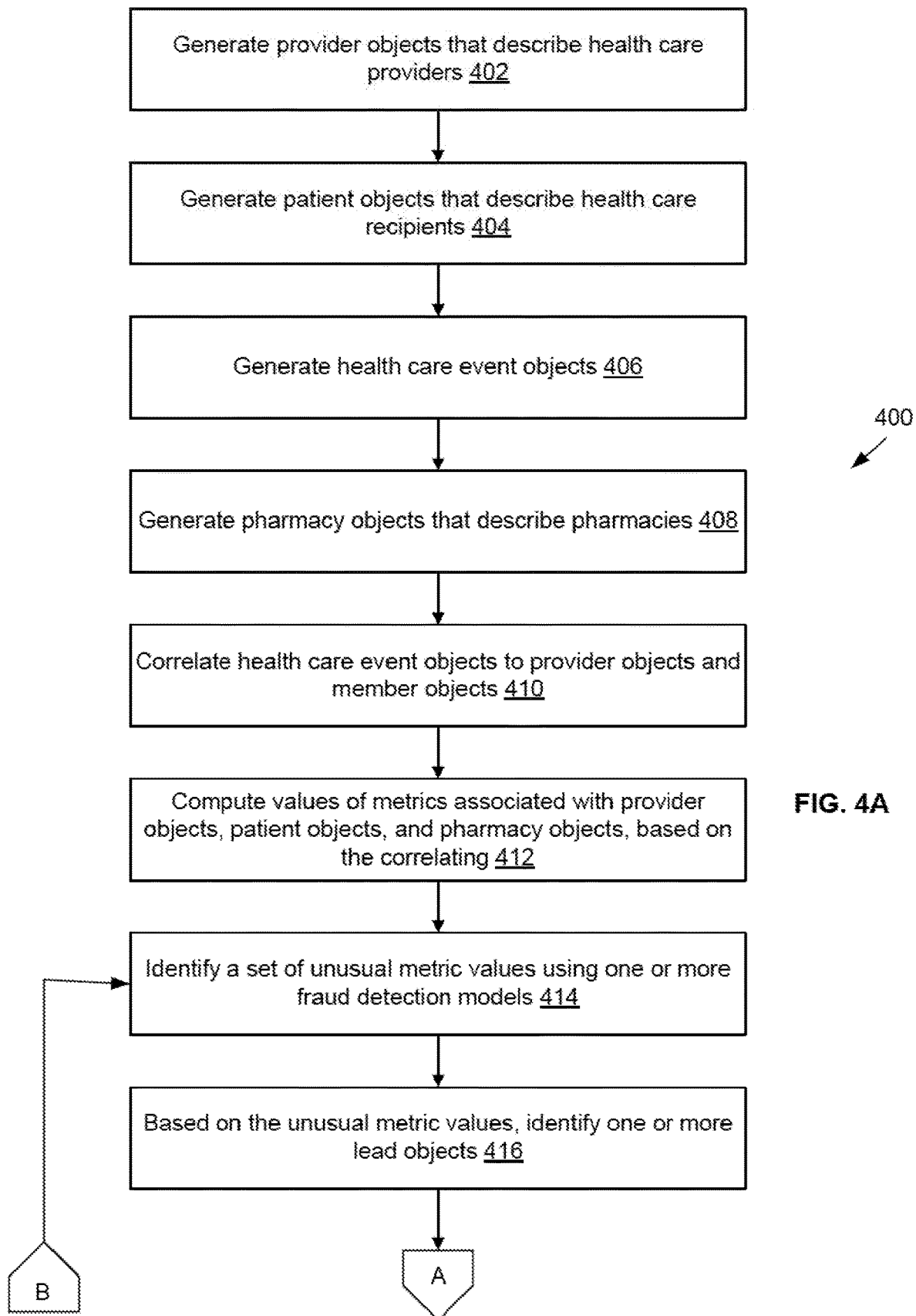
FIGS. 4A-4D illustrate example flow diagrams for performing fraud lead generation and presentation in the system of FIG. 1 according to some embodiments.
Figure 4B:
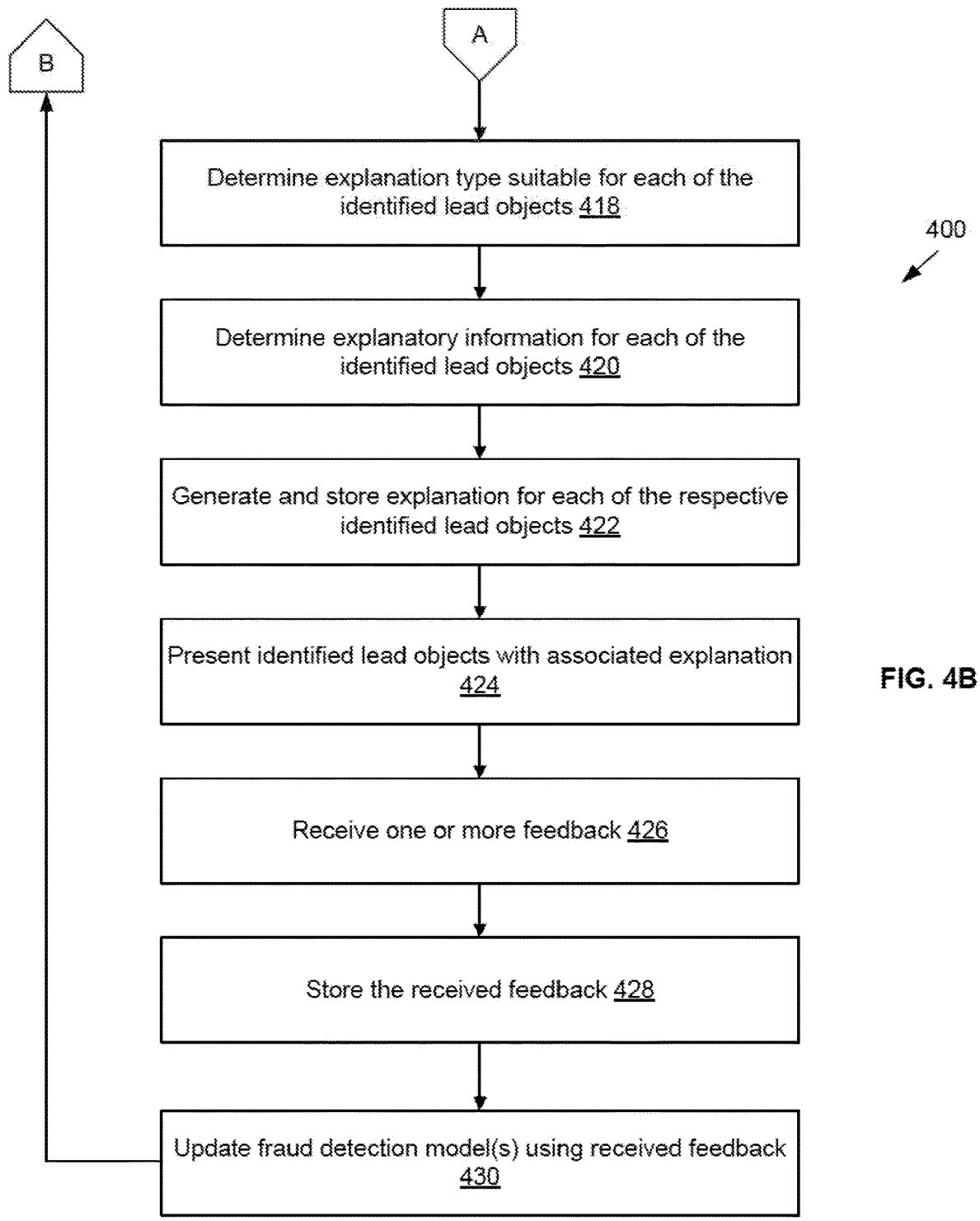

FIGS. 4A-4B illustrate a flow 400 for automatically identifying leads and generating associated explanation information, according to an embodiment. In an embodiment, each of the processes described in connection with the functional blocks of FIGS. 4A-4B may be implemented using one or more computer programs, other software elements, and/or digital logic in any of a general-purpose computer or a special-purpose computer, while performing data retrieval, transformation and storage operations that involve interacting with and transforming the physical state of memory of the computer. Flow 400 of FIGS. 4A-4B is described below in conjunction with the objects and components of FIG. 3.

Block 402 comprises the data import component 308 generating provider objects 312 that describe different health care providers. Data for the provider objects may be obtained, for example, from claims submissions of providers to insurers, who then provide the data to a computer system that implements the techniques herein. A health care provider may be any entity that provides health care services. Health care providers may include organizational entities, also referred to as facilities or institutions, such as hospitals and clinics. Health care providers may also or instead include individual practitioners, also referred to as health care workers, such as doctors and dentists. In some cases, such as in the case of solo practitioners, an individual practitioner may also function as an organizational entity.

In an embodiment, there are different types of provider objects that represent individual practitioners as opposed to organizational entities. In an embodiment, different types of provider objects may comprise data collected concerning the same providers from different sources. In an embodiment, different types of provider objects may comprise data collected concerning the same providers while those providers are functioning in different roles. For example, a single doctor may correspond to a prescriber object that stores data collected concerning the doctor while in his capacity as a prescriber of drugs, one or more specialist objects that store data collected concerning the doctor while in his capacity to perform certain specialized procedures or evaluations, and/or a practitioner object that represents data collected from the doctor while in his role as a provider generally. Alternatively, a doctor may be represented by a prescriber object, and then associated with a facility object for a facility at which the doctor is employed. In an embodiment, there may be only one type of provider object, and all data related to all of the roles of a doctor/practitioner may instead be collected under the umbrella of this single type of provider object.

Block 404 comprises the data import component 308 generating patient objects 314 that describe recipients of health care. In an embodiment, different types of patient objects may comprise data collected concerning the same providers from different sources. For example, a single person may be represented by a member object comprised of data collected by an insurer that sponsors a health plan of which the person is a member, but also be represented by separate patient objects comprised of data collected in association with different providers, and/or customer objects comprised of data collected from a pharmacist. In an embodiment, different types of patient objects do not necessarily correlate to sources, but rather to roles associated with a patient when data is collected, such as a plan member, or a pharmacist customer. In an embodiment, data related to all of the roles of a patient may instead be collected under the umbrella of a single type of patient object.

Block 406 comprises the data import component 308 generating health care event objects 318 that describe one or more of: health care claims, prescriptions, medical procedures, or diagnoses. For example, an event object may be generated for each log entry in one or more logs from providers, insurers, and/or pharmacies, or based on claims submissions to insurers. There may be multiple types of event objects for some or all of claims, prescriptions, procedures, and diagnoses. For example, there may be different event object types for medical claims and prescription claims. Or, there may be a single event object type comprising a type field that classifies each event. Other event types may also be modeled, such as instances of fraud. Different embodiments may feature different combinations of events.

Block 408, which may be optional in some embodiments, comprises the data import component 308 generating pharmacy objects 316 that describe pharmacies. Depending on the embodiment, there may be different types of pharmacy objects to represent different types of pharmacies. Data for pharmacy objects may be obtained directly from pharmacies or their owners, or from claims data of insurers.

Block 410 comprises the correlation component 340 correlating event objects to provider objects, patient objects, and/or pharmacy objects. For convenience, the term entity may subsequently be used to refer to any one of a provider, patient, or pharmacy, and the term entity object may thus be used to refer to any object comprising data that represents such an entity. Each correlated event object is resolved to at least one of the provider objects, patient objects, or pharmacy objects (if generated) by comparing one or more attributes of the event object, such as an identifier of an entity involved in the event, to corresponding attribute(s) of the provider objects, patient objects, or pharmacy objects. For example, a prescription event object may comprise fields that identify objects representing the practitioner who wrote the prescription, or an associated facility. As another example, a claim event may comprise fields that identify a member object and a facility object.

In embodiments where different types of provider objects and/or patient objects may exist for the same entity, block 410 may also comprise correlating those objects using any suitable entity resolution technique. For example, a practitioner object may be correlated to a prescriber object using a government identifier, or a unique combination of attributes such as name, location, and age. Once objects have been correlated to a same entity, a unique system identifier for the entity may be created, and added as an attribute to each object correlated to that entity. For the purposes of the subsequent analyses, objects resolved to a single entity may be temporarily merged into one or more logical provider or patient objects. Or the objects may remain separated, but linked to each other by relationships.

A relationship is a data construct that links two or more objects in association with a defined relationship type. In an embodiment, block 410 optionally comprises generating relationships based on the correlating. At least some of the event objects may be correlated to multiple entity objects. For example, a prescription object may be correlated both to the prescriber object representing the doctor who wrote the prescription, and a patient object representing the patient for whom the prescription was written. The event objects may thus be used to derive relationships between entities that reflect services rendered by a first entity in the relationship on behalf of a second entity in the relationship, such as "wrote a prescription for" or "filled a prescription at" or "received a diagnosis at." In an embodiment, a relationship may further include attributes that link the relationship to specific event(s) from which the relationship was derived and/or that count the number of associated events.

Block 412, which is optional, comprises the metric generation component 342 computing values of metrics associated with the provider objects, the patient objects, and the pharmacy objects, based on the correlating. Block 412 may comprise various aggregations of the data associated with the provider objects, patient objects, and/or pharmacy objects. In some embodiments, one or more of the particular metrics for which values are calculated may be variables within the particular fraud detection model(s) used in block 414. Some of the metrics may be derived to represent features, properties, or characteristics of the various objects. Other metrics may represent features, properties, or characteristics of relationships between objects. Yet other metrics may be generated for a variety of other purposes.

A first example type of metric for a particular entity object (or a group of entity objects) involves counting correlated event objects of certain types and/or that have certain qualities. A second example type of metric involves summing or averaging certain attributes of certain types of correlated event objects and/or of correlated event objects having certain qualities. A third example type of metric involves computing standard deviations for other metric values across groups of entities and/or geographic areas. A fourth example type of metric involves calculating various functions of certain attributes of certain correlated event objects. A fifth example type of metric involves calculating the percentage of correlated event objects of a certain type that have certain attribute value(s). A variety of other types of metrics of varying complexity are also possible. For example, various metrics may be formulated to attempt to identify any of the fraudulent behaviors described herein.

Some metrics may be time-sensitive. For example, some metrics may pertain to events of a recent time period such as the last month or year, while others may pertain to designated time periods such as Q3 2007. The metrics for a particular entity may also be based on metrics or attributes associated with entities to which the particular entity is related. For example, a metric for a practitioner may count the number of the practitioner's patients who have a certain quality such as a history of drug abuse.

Block 414 comprises applying one or more fraud detection models to some or all of the objects generated in blocks 402-410. In an embodiment, block 414 may comprise inputting the values of various properties or fields of an object, and/or metrics calculated in association with an object, into parameters of the fraud detection model(s). Block 414 then comprises performing various calculations based thereon. For instance, in an embodiment, a fraud detection model may comprise one or more mathematical functions having "signals" that correspond to such parameters, and optionally weights associated with the signals. The weights may be manipulated by hand and/or via various machine learning mechanisms based on feedback as described herein. The function(s) may calculate score(s) that quantify how likely it is that an object is associated with fraudulent activity. Optionally, these score(s) may then be compared to threshold values and/or knowledge bases in order to classify the object. Many other suitable types of fraud detection models may also exist, and are described subsequently.

In yet other embodiments, relatively simple rule-based models may also or instead be utilized (e.g. filling more than a certain number of prescriptions over a period of time, etc.).

For example, a rule-based model based on mutual information may be utilized (referred to as outlier detection #2 in Table 1 below). Mutual information is a statistical quantity (e.g., a score) and may be computed on a count of a number of procedures between a member and a provider (e.g., a number of knee surgeries a member has received at the provider), where the count information is derived from the medical claims data. The mutual information between providers and members may be computed for each provider. The mutual information score for each provider may then be compared to determine providers (or provider objects) that are outliers. Generally, a low mutual information score may indicate that a provider is not tailoring treatment to a member, but is rather offering the same treatment to most or all members. Thus, a provider (or provider object) may be considered an outlier if a mutual information score associated with the provider (or provider object) is less than a threshold value. The threshold value may not be a set value, but rather may be based on the other mutual information scores of the other similar providers (because, for example, some providers may always perform the same procedures given the nature of the specialty of the providers). For example, the threshold value may be computed by identifying a median mutual information score for all providers that offer the first procedure, a mutual information score that represents a boundary of a first quartile of mutual information scores for all providers that offer the first procedure, a mutual information score that represents a boundary of a third quartile of mutual information scores for all providers that offer the first procedure, measuring a spread between the mutual information score that represents the boundary of the first quartile and the mutual information score that represents the boundary of the third quartile, determining a multiple of the spread (e.g., 2 times the spread), and identifying the threshold value as a multiple of the spread below the median mutual information score (e.g., if the median mutual information score is 5, the spread is 1.5, then the threshold value may be 2, which is 2 times the spread less than the median mutual information score). The determined provider (or provider object) outliers may then be classified as being associated with fraudulent activity.

As another example, a rule-based model based on prescription claims data may be utilized (referred to as outlier detection #3 in Table 1 below). The prescription claims data may be analyzed to determine what prescriptions have been assigned to a member and how many providers issued the same prescription to a single member. If the number of providers exceeds a threshold value (where the threshold value may be dependent on the prescription that was issued), then the member (or member object) associated with the issued prescription may be classified as being associated with fraudulent activity.

Block 416 comprises, based on how each object is classified and/or scored by the fraud detection model(s), the lead identification component 344 identifying one or more lead objects (also referred to as leads, fraud leads, or suspected fraud leads). Depending on the embodiment and/or implementation, in implementations in which more than one fraud detection model is utilized, an object may be a lead if even just one of the fraud detection models classified it as such, if more than a certain number of fraud detection models classified it as such, and/or based on a function of scores calculated by the models. The lead object(s) include one or more of: a particular provider object, a particular pharmacy object, and/or a particular member object. In some embodiments, lead objects may also include event objects, such as particular health care claims. However, in other embodiments, only objects that represent entities are identified. The lead objects may not necessarily include all objects identified by the applied data model(s). For example, certain potential lead objects may be filtered based on business rules. Or, the potential lead objects may be filtered based on a ranking process to prioritize an investigation.

In an embodiment, a lead object is flagged within a database, and an investigative analyst may later look for any objects that have been flagged. Different objects may be flagged differently to indicate that they should be investigated by an investigator having different specialties. For example, different object types and/or suspected fraud types may be better suited for investigation by different types of analysts. In an embodiment, an email identifying lead objects may be generated. Any other suitable mechanisms may be used for identifying the lead objects to analysts.

In an embodiment, blocks 402-416 comprise activities associated with fraud lead generation. In an embodiment, at least blocks 414-416 occur in response to a request from an analyst to an analysis module. The analysis module visually reports the leads in a user interface area, from which the investigator may immediately launch an investigation using techniques such as described herein.

Once one or more lead objects or leads are identified and prior to making these identified leads available to analysts, fraud lead explanation generation-related activities occur to augment the identified leads, according to an embodiment. Rather than overwhelming analysts with a large number of identified leads, which may number in the hundreds or thousands, analysts may benefit from also having information about how and/or why some or all of the identified leads is suspected of being associated with fraudulent activity. At the same time, however, analysts may not be well versed in modelling techniques, pattern recognition techniques, statistical analysis, or other techniques used by the system 300 to surface the identified leads. Thus, a balance is sought in the type of information provided with each of the respective identified leads. Information that is readily understandable and in context with the particular identified lead that analysts would consider to be helpful actionable signals to assess the particular identified lead.

Block 418 comprises the lead-relatedness calculation component 360 determining the type(s) of explanatory information suitable to provide with each of the identified lead objects. Example types of explanatory information include, but are not limited to, a "similar leads"-type of explanation, a "distinguishing metrics/features"-type of explanation, and/or a "statistical"-type of explanation. One or more explanatory information item may be associated with a given identified lead and/or may be in a natural language format. For example, if a lead object is identified based on the outlier detection #2 fraud detection model described herein, then the explanatory information may include template text and specific values associated with the identified lead object that are auto-populated into the template text that describe the meaning of a mutual information score (without actually providing the mutual information score, which may be meaningless to a fraud analyst). The meaning of the mutual information score can, for example, be described with respect to percentage values. The explanatory information may include a percentage of members that received a first procedure from the provider associated with the lead object, a percentage of members that received a second procedure from the provider associated with the lead object, and so on. Providing a visualization of these percentages may illustrate that, for example, the provider is providing the same multiple services to a large number of members. An example of such explanatory information is illustrated in FIG. 5, as described below. Depending on the particular fraud detection model used to identify a given lead, the availability of other leads similar to the given lead that were previously labelled as positive leads by analysts, or other factors, particular type(s) of explanatory information may be more meaningful than others. For example, if a sufficient number of other leads were previously labelled as fraud by analysts, and a nearest neighbor analysis reveals that a given identified lead is sufficiently similar to one or more of these fraud-labelled other leads, then a suitable explanatory information type may comprise a similar lead-type of explanation. The explanation may, for instance, identify these previously fraud-labelled leads, describes the relatedness or similarity of the given identified lead to these previously fraud-labelled leads, and pointers to look into the same or same types of items that were previously investigated for these previously fraud-labelled leads. As another example, if there are an insufficient number of other leads previously labelled as fraud, then a similar lead-type of explanation may not be possible. Instead, suitable explanation types may comprise statistical-type of explanation or the distinguishing features in the model used to identify a given lead. In an embodiment, the determination of block 418 is optional, and the same explanation type may always be given.

Block 420 comprises the lead-relatedness calculation component 360 determining explanatory information appropriate for each of the identified lead objects. For a similar lead-type of explanation, a nearest neighbor identification technique using weighted distances may be used to identify one or more previous leads of sufficient similarity to the identified lead. Nearest neighbor objects, referred to herein as "nearest neighbors," may be those previous leads within a certain distance or similarity to the given lead, and/or those which were identified as leads using the same fraud detection model(s) as were used to find the identified lead. As an example, if the identified lead was found using a supervised model, to be described in detail below, then the nearest neighbors identified may be examples of fraud-labelled leads within the training data used to train the supervised model. Alternative nearest neighbor identification techniques may include, without limitation, the k-nearest neighbor algorithm (KNN), approximate nearest neighbor algorithms, and/or other suitable nearest neighbor techniques known within the art. These techniques may involve calculations based on comparing properties and/or metrics associated with the identified lead and properties and/or metrics associated with previously identified leads. While in an embodiment, only nearest neighbors that were positive leads are selected, in other embodiments, a nearest neighbor may be any identified lead, and the disposition towards that lead (positive or negative) may be indicated to the user.

For a distinguishing metrics/features-type of explanation, information about the particular model used to find the identified lead is provided. For instance, those metrics or features included in the model having the highest weights or contribution in deciding that the given identified lead is suspected of fraud may be identified and described. As an example, models using logistic regression techniques include assignment of various weights to metrics included in the models. For a statistical-type of explanation, information about data distribution, mean, median, p-values, and/or other various statistics related to the metrics and/or properties of the object are given.

Block 422 comprises the lead explanation generation component 362 generating or configuring the explanation associated with each of the respective identified lead objects based on the determined explanatory information in block 420. The lead explanation generation component 362 optionally stores the generated explanation and indicates association with a given identified lead, such as in lead annotations 334. The generated explanation is also referred to as explanatory information, fraud lead explanation, fraud lead supplemental information, fraud lead insight, and the like.

Block 424 comprises the user interface component 370 presenting a set of the identified lead objects, with respective associated explanations, typically in response to a request by one or more analysts to view identified lead objects. For instance, a server 102 may generate a list of the leads in the form of a web page, and send the web page to a client 106 for viewing. Or, as another example, the server may generate other suitable data indicating the set of lead objects, and client 106 may utilize any of a variety of data visualization techniques, such as maps, node-based graphs, and so forth, for presenting the lead objects. In an embodiment, the identified lead objects with respective appended explanation may automatically be provided to analysts' workspaces without prompting by analysts. The set of leads, in some embodiments, may be a ranked list based on one or more ranking criteria, such as highest to lowest fraud probability (e.g., based on scores from the fraud detection models and/or other ranking functions), leads associated with unpaid claims before paid claims, leads found using a particular model over another model, and the like.

The explanation comprises graphical and/or textual information. The explanation comprises one or more information items or independent signals. The explanation may be organized in any number of ways, such as a dossier of the associated identified lead. The information conveyed may, depending on the embodiment and/or explanation type chosen, identify the model used to surface a lead, explain certain metrics/features of the lead, identify previously denoted positive or investigated leads similar to the present lead, provide statistical information or arguments about the lead, and/or otherwise relate the lead to information that is familiar, trusted, and/or readily understandable to analysts. In an embodiment, the presented information is configured so as not to overwhelm analysts. The goal is not necessarily to provide as much information as possible, such as exposing all the details of the model and statistical analysis performed to arrive at the lead. Rather, it is to provide information that is readily relatable to analysts and provide guidance as to where and/or what to look for to assess the lead. The presented information may thus comprise an explanation by example.

For example, the explanation may include one or more example leads that are similar to the currently identified lead, such as: "Providers x, y, and z were previously labeled as frauds. Based on the weights we learned, this new lead is a nearest neighbor to providers x, y, and z." This relates the currently identified lead to lead(s) that analysts previously determined to be fraudulent. The explanation may also include guidance indicating items (e.g., items A, B, and C) looked at by analysts to make the fraud determination for the example lead(s), such as: "When reviewing the new lead, suggest looking into the same items A, B, and C that analysts looked into for providers x, y, and z to expose the fraud." This provides a starting point for analysts to investigate the currently identified lead.

As analyst(s) review the identified lead objects and associated explanations, analyst(s) may label or flag certain of the identified lead objects as being positive leads, investigated leads, or having other label type(s); provide reasoning for labeling a lead a certain way; prepare notes about certain of the identified lead objects, and otherwise provide feedback-type of data in the course of assessing the identified lead objects to determine what further action, if any, to take on certain of the lead objects. One or more of such feedback-type of data is received by the user interface component 370 in block 426. The received feedback-type of data is stored by the user interface component 370 in feedback data 330 in block 428.

Block 430 comprises updating the fraud detection model(s) that were applied in block 414 using the received feedback in block 426. Block 430 may involve, for instance, re-training the fraud detection models using the new feedback data as part of a training set. The training may involve, for instance, calculating new weights for signals using any suitable machine learning technique. The exact nature of the training will vary from model to model, using any suitable training technique for the relevant model.

After incorporating the feedback in block 430, flow 400 returns to block 414 to identify future sets of fraud-suspected leads based on the improved knowledge. As discussed in detail below, the feedback data is used to improve existing fraud detection models and/or identify new fraud detection models over time.

Flow 400 is but one example technique for identifying leads through metrics generated using data organized in accordance to a health care data model and for presenting the identified leads with associated explanation. Other flows may include fewer or additional elements in varying arrangements.

3.3 Improvements to Existing Fraud Detection Models

Figure 4C:
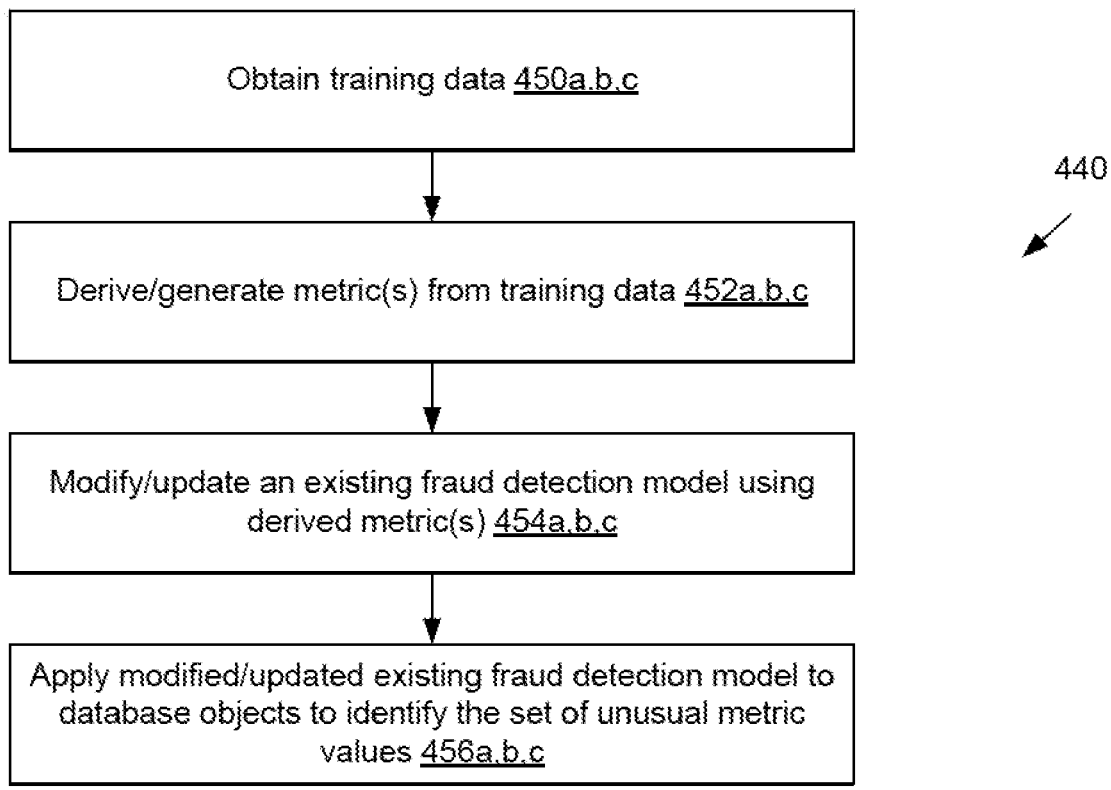

FIG. 4C illustrates a flow 440 for improving or refining one or more of the existing fraud detection models used by system 300, according to an embodiment. In an embodiment, flow 440 may be utilized in part to perform blocks 414, 416, and 430 of FIG. 4B. However, flow 440 may be utilized for fraud detection flows other than that of flow 400. In an embodiment, each of the processes described in connection with the functional blocks of FIG. 4C may be implemented using one or more computer programs, other software elements, and/or digital logic in any of a general-purpose computer or a special-purpose computer, while performing data retrieval, transformation and storage operations that involve interacting with and transforming the physical state of memory of the computer. FIG. 4C is described below in conjunction with the objects and components of FIG. 3.

In an embodiment, fraud detection models perform classification. Namely, fraud detection models perform the task of classifying entities in the health care data (e.g., entities such as providers, members, pharmacies, or claims) as belonging to a particular category from among a plurality of categories. For instance, if the classification is of provider entities that have submitted health care claims, which are stored in the repositories 310, the classification task may be to determine whether each of the provider entities is suspected of fraudulent activity (e.g., of a category "yes fraud") or not suspected of fraudulent activity (e.g., of a category "no fraud"). However, because detecting fraud may not be a clear cut yes or no proposition, the classification task may comprise identification of those provider entities with the highest likelihood of suspected fraudulent activity—comprising the identified leads. Whether the remaining provider entities are actually not frauds or merely indeterminate may not be known. In some embodiments, the classification task may simply involve calculating a score reflecting the likelihood of certain classification(s).

In order to improve classification of these remaining provider entities, and because fraud schemes evolve over time, improvements to one or more of the existing fraud detection models is implemented using machine learning techniques, according to an embodiment. In particular, supervised and/or unsupervised machine learning techniques may be used to iteratively train a fraud detection model over time. The fraud detection model is trained using one or more sets of training data, which comprise data of known characteristics or classification (e.g., provider entities known or confirmed to be frauds).

In an embodiment, an existing fraud detection model based on logistic regression techniques (also referred to as a logistic regression model) is improved, trained, or seeded using feedback data obtained in block 426 of FIG. 4B. Block 450a comprises the training data translation component 346 of FIG. 3 obtaining training data from feedback data 330. Training data (also referred to as training data set, example leads, or example data) may comprise, for instance, data indicating previous leads and final dispositions towards those leads (e.g., known to be fraudulent, known not to be fraudulent, indeterminate, etc.). For examples, the training data may simply indicate a subset of the previously identified leads deemed to be frauds by analysts—those leads labelled or flagged as positive leads. Training data may also comprise, or in the alternative be, a subset of the previously identified leads escalated by analysts for investigation and which were investigated—those leads labelled or flagged as investigated leads. There may be instances where a positive lead may not necessarily be an investigated lead. In some embodiments, the positive and/or investigated leads used as training data are leads identified using the same fraud detection model, albeit an earlier iteration, as the particular existing model to be trained or improved. Training data may further include lead annotations 334 and/or other explanations provided by analysts and/or investigators as to why these leads were found to be fraudulent.

In an embodiment, only a sub-subset of the positive and/or investigated leads may be used as the training data for active learning purposes. Only those positive and/or investigated leads that may help the most in speeding the rate of convergence in machine learning may be used rather than all of the positive and/or investigated leads. For instance, in an embodiment, the most helpful leads may be the boundary or near-boundary leads—those leads for which it is unsure whether the leads are fraudulent, but for which feedback from the analyst would improve the model's accuracy the most. In another embodiment, a pre-defined number of the best positive and/or investigated leads may be used as the training data.

Block 452a comprises the training data translation component 346 deriving one or more metrics from the training data. The derivation comprises performing a translation, conversion, or other transformation operations to quantify and express the fraudulent characteristics of leads in the training data into particular metrics, metric values, weights of certain metrics, and/or combination of metrics for inclusion in the existing model of interest.

Block 454a comprises the model refinement component 348 modifying or updating the particular existing model using the metric(s) derived in block 452a. A model is one or more mathematical function(s) of a particular combination of particular signals (e.g., metrics or properties), in which the signals may be given particular weights relative to each other. A plurality of signals is expressed in the existing model. As such, the modification or updating may comprise assigning different weights to various signal(s), and/or otherwise adjusting the impact of the signals expressed in the existing model.

In an embodiment, users may optionally add new signals to the model to reflect newly available metrics, properties, or other data. In an embodiment, metrics are added to the existing model but not removed. Those metrics found to be less relevant may be assigned a lower weight than before to account for the decrease in importance. Thus, the existing model is improved by taking into account, and learning from, known dispositions towards particular leads from among the leads that were previously only suspected of fraud by the previous iteration of the existing model.

The updated existing model is used in block 456*a* by the lead identification component 344 to classify objects and identify leads, as described above in connection with blocks 414 and 416. Note that if the particular model is considered to be in training or testing phase only (e.g., pre-production version), then the leads identified from such model in block 416 are labelled as test leads or equivalent to denote that they are not actual leads identified for regular assessment and possible investigation.

For example, the logistic regression model is used to identify ten suspicious providers from the database of health care data during a first week. The assumption would appear to be that the remaining providers are not suspected of fraud. In actuality, however, it is more likely that one or more of the remaining providers are also potentially fraudulent, but the model is unable to find them. In order to train the logistic regression model to find one or more of these remaining providers, as well as new providers added to the database that are also likely fraudulent, the model is used to identify ten suspicious providers per week at each of the first week, second week, etc. Analysts assess the identified provider leads from the first week to determine which are fraudulent. Analysts label or flag the providers accordingly and, in some cases, also provide an explanation of why a particular provider is fraudulent or not. The analysts' assessments of the identified provider leads from the first week are interpreted and fed back into the model. When the model identifies ten suspicious providers for the second week, the version of the model used to make the identification is a version that is trained and updated from the version used during the first week based on the analysts' assessment of the provider leads identified in the first week. The current version of the model is iteratively improved, "seeded" by positive, investigated, example, and/or known leads associated with a previous version of the model.

In another embodiment, an existing fraud detection model based on nearest neighbor detection techniques (also referred to as a nearest neighbor model), such as KNN, is improved, trained, or seeded using feedback data obtained in block 426 of FIG. 4B.

Block 450*b* of FIG. 4C comprises the training data translation component 346 obtaining training data from feedback data 330, similar to the description above with respect to block 450*a*. In block 450*b*, the training data can be leads identified using the same or different models than the nearest neighbor model.

Block 452*b* comprises the training data translation component 346 deriving one or more metrics from the training data, similar to the description above with respect to block 452*a*.

Block 454*b* comprises the model refinement component 348 modifying or updating the existing nearest neighbor model using the metric(s) derived in block 454*b*, similar to the description above with respect to block 454*a*. The derived metric(s) define a metric space (also referred to as a feature space) in which known fraudulent leads and yet-undetected fraudulent leads are clustered together. The features of the positive and/or investigated leads, which are defined in the corresponding derived metrics, provide a starting point from which to search for other leads having similar features (e.g., the nearest neighbors) and may also define a permissible maximum distance from the starting point for a lead to be considered a nearest neighbor.

Block 456*b* comprises the lead identification component 344 applying the modified/updated existing model to database objects to identify the set of unusual metric values, similar to the description above with respect to block 456*a*. The updated nearest neighbor model uses or implements the metric space to find new leads that are closest in cosine distance to the previously known fraudulent leads. The new leads that are identified using this model are outputted in ranked order relative to each other. As an alternative, if the updated nearest neighbor model is applied to leads identified from one or more of the other models, as opposed to database objects as a whole, then the output may be a re-ranking of these identified leads that is more accurate than their original ranking order.

In still another embodiment, an existing fraud detection model based on network detection techniques (also referred to as a network model or network based model) is improved, trained, or seeded using feedback data obtained in block 426 of FIG. 4B.

Block 450*c* of FIG. 4C comprises the training data translation component 346 obtaining training data from feedback data 330, similar to the description above with respect to block 450*a*. In block 450*c*, the training data can be leads identified using the same or different models than the network model.

Block 452*c* comprises the training data translation component 346 deriving one or more metrics from the training data, similar to the description above with respect to block 452*a*. In some embodiments, the previous leads may establish the starting point of the search for other leads. The derived metrics may also define what network relationship(s) to look for between pairs of entities (or a cluster of entities) and/or the suspected fraudulent features to look for between pairs of entities. For example, the network relationship and fraudulent activity of interest may focus on re-use of stolen or sold patient social security numbers, in which an unusually high number of patients (as identified by their social security numbers) shared between pairs of providers is indicative of a potential network of fraudulent providers. Individually, each of the providers may not be suspected of fraud; however when their network of other providers and collective activities of these provider networks are taken into account, a pattern of fraud may surface. The network-centric technique may use network detection techniques practiced in the social networking area.

Block 454*c* comprises the model refinement component 348 modifying or updating the existing network model using the metric(s) derived in block 454*c*, similar to the description above with respect to block 454*a*.

Block 456*c* comprises the lead identification component 344 applying the modified/updated existing model to database objects to identify the set of unusual metric values, similar to the description above with respect to block 456*a*. Provider-member relationships and provider-provider relationships form networks that are highly informative and can be used to uncover fraudulent entities. Relationships may comprise, without limitation: shared members, co-occurrence in same investigation, share same National Provider Identifier (NPI), share same phone number, share same referring doctor, share same address, or non-medical claim based co-occurrence.

Continuing the example above, the updated network model starts with a known "bad" provider (e.g., previously identified positive and/or investigated provider lead), determines the "bad" provider's network(s), and identifies one or more additional "bad" providers in the known "bad" provider's network(s) that share a certain number of the same member/patients between them. A provider-provider graph is conceptually constructed where each node of the graph represents a provider and edges of the graph represent jaccard distances of patients shared between providers to detect the one or more additional "bad" providers.

In other embodiments, fraud detection models based on other classification, statistical, and/or pattern recognition techniques such as, but not limited to, neural networks or random forest models can be trained or improved over time using the iterative processes described herein.

3.4 Formulation of New Fraud Detection Models

Figure 4D:
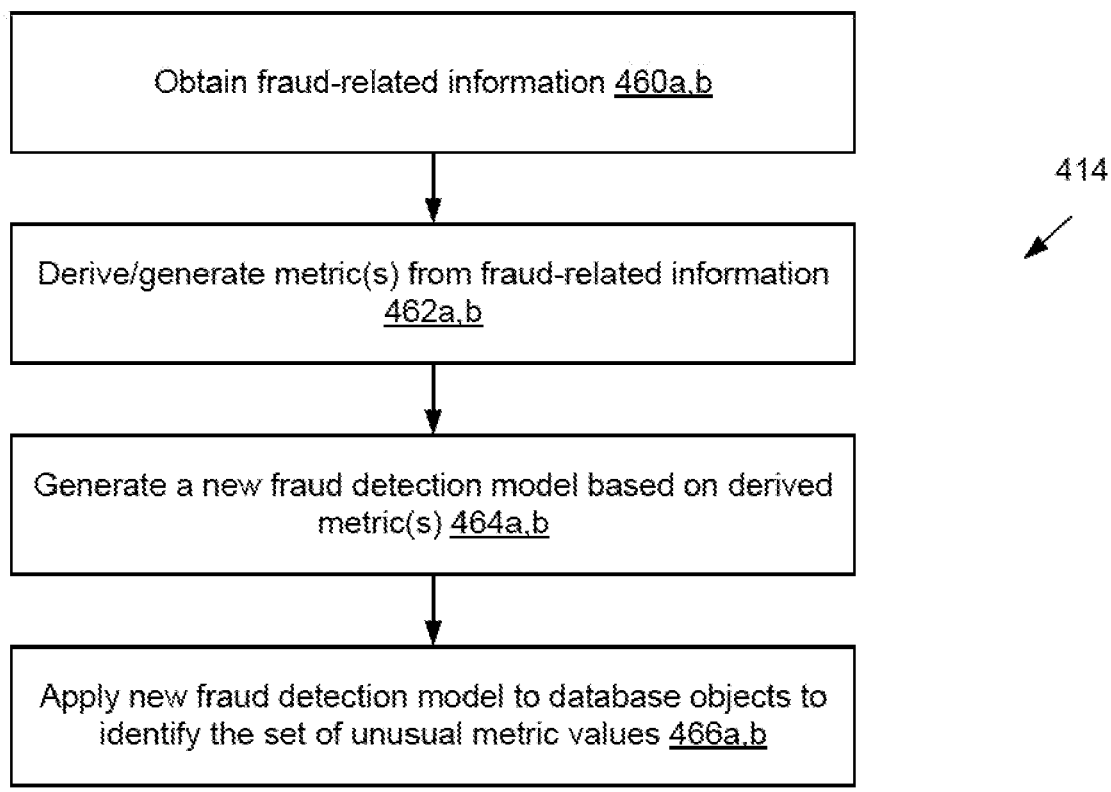

FIG. 4D illustrates additional details of block 414 of FIG. 4A, and in particular, details pertaining to formulation of one or more new fraud detection models used by system 300, according to an embodiment. In an embodiment, each of the processes described in connection with the functional blocks of FIG. 4D may be implemented using one or more computer programs, other software elements, and/or digital logic in any of a general-purpose computer or a special-purpose computer, while performing data retrieval, transformation and storage operations that involve interacting with and transforming the physical state of memory of the computer. FIG. 4D is described below in conjunction with the objects and components of FIG. 3.

In an embodiment, a new fraud detection model is formulated based on domain- and/or expert-based knowledge (also referred to as a domain-based model or heuristics rule-based model). Block 460*a* of FIG. 4D comprises the metric provider component 350 of FIG. 3 obtaining fraud-related information from machine and/or human sources. Fraud-related information comprises, but is not limited to: domain-based knowledge from analysts, intuitive-based knowledge from analysts, experience-based knowledge from analysts, fraud tips from news articles, conferences, or persons, any of the above from subject matter experts, and other features or properties of a potential fraud scheme. The fraud-related information may be obtained from feedback data 330, in some embodiments. Fraud-related information can be insights to aspects or features of a fraud scheme that were previously unknown.

Block 462*a* comprises the metric provider component 350 deriving one or more metric(s) from the fraud-related information. Fraud-related information can be specific articulation of one or more metrics/features indicative of fraudulent activity, such as an analyst noticing that a particular feature is present in a high proportion of the leads that she or he investigates. Or the fraud-related information can be less well-defined that a machine and/or human converts, translates, or otherwise transforms into one or more metrics suitable for use in fraud detection models. Additionally, as discussed above with respect to block 452*a*, derivation of metrics may also include determining values of one or more metrics, weights for one or more metrics, the particular combination of one or more metrics, and other variables comprising the model.

Block 464*a* comprises the new model component 352 generating or formulating domain-based model based on the derived metric(s). In some embodiments, all of the metrics expressed in the model are obtained from non-training data sources. In other embodiments, the derived metric(s) can be included in a model deemed to be incomplete, and as such, may be considered to be improvement of an existing model. In either case, incorporation of fraud-related information provided by analysts, experts, tips, and/or other sources provides additional ways to create models that may supplement and/or be independent of models formulated using known positive and/or investigated leads.

Block 466*a* comprises the lead identification component 344 applying the new model to database objects to identify the set of unusual metric values, similar to the description above with respect to blocks 456*a, b, c*.

In another embodiment, a new fraud detection model is formulated based on one or more of the outlier detection techniques (also referred to as an outlier model) described in Table 1 below. Block 460*b* comprises the metric provider component 350 obtaining fraud-related information from machine and/or human sources, similar to the description above with respect to block 460*a*. Alternatively, block 460*b* may be optional if the metrics to use in the model are known. For example, metrics corresponding to positive and/or investigated leads from block 452*a,b,c* may comprise at least some of the known metrics.

Block 462*b* comprises the metric provider component 350 deriving one or more metric(s) from the fraud-related information, or if metrics are known, further configuring the metrics to generate the derived metrics. In an embodiment, all known metrics and variations of metric values, ranges, or other statistical manipulation of the known metrics comprise the derived metrics. For each metric/feature, a corresponding metric/feature list is generated by calculating different aggregates of the metric/feature such as: a count, median, mean, variance, maximum, minimum, entropy, temporal trends in any of the foregoing, and the like. The number of metrics/feature can number in the hundreds, thousands, or tens of thousands.

Block 464*b* comprises the new model component 352 generating or formulating the outlier model based on the derived metrics. The outlier model is built to calculate a distribution of the probability of occurrence of a combination of one, two, or more particular derived metrics in the health care data in the database. All combinations of one, two or more derived metrics are considered, each combination corresponding to a respective distribution. An example combination may be to discover the distribution of amount billed by providers of a particular specialty, for a particular procedure, per patient over a certain time period. Another example combination may be to discover the distribution of amount billed by providers of a particular specialty, for a particular diagnosis, over a certain time period.

Block 466*b* comprises the lead identification component 344 applying the new model to database objects to identify leads, similar to the description above with respect to blocks 456*a, b, c* and block 466*a*. In an embodiment, a distribution is calculated for a pair of two of the derived metrics, and then outliers in the distribution are identified. The outliers comprising, for example, those entities associated with a certain standard deviations from the mean, such as of the amount billed. This is repeated for every unique combination of pairs of derived metrics. Then the top outliers from across all of the distributions comprise the identified leads.

Identification of statistical outlier cases may also provide insight into novel fraud schemes that were previously unknown. The outlier model permits surveying distribution of the database objects in a comprehensive manner so as to surface statistical outliers that may otherwise not be detectable.

As seen from the discussion above, the distinction of generating new models, refining existing models, and/or identifying fraud suspected leads is not necessarily clear cut. One or more of these functions may be blurred in systems that incorporate feedback and employ iterative processes as described herein. To the extent that distinctions are introduced, the distinctions may be artificial constructs to simplify describing various aspects of the system 100 and/or 300.

3.5 Fraud Detection Model Implementation Examples

In an embodiment, various fraud detection models can be implemented as follows to identify certain fraudulent activity and/or entities.

TABLE 1

| Model | Potential fraud scheme | Mode implementation |
|---|---|---|
| Outlier detection #1 | Egregious billing Violation of certain provider rules | Identify entities<br>Aggregate entity associated data by a common or standard factor<br>Aggregation using, for example, an arithmetic function<br>Segment data by, for example, specialty, procedure, region, and/or the like<br>Potential bimodal distribution detection |
| Outlier detection #2 | Providing unnecessary procedures | Identify entities<br>Determine, for one or more entities, the types of procedures performed<br>Determine, for one or more types of procedures and for one or more entities, the percentage of members that receive the respective procedure performed by the respective entity<br>Compare, for one or more types of procedures, the percentage of each entity that performs the respective procedure |
| Outlier detection #3 | Provider shopping | Identify members<br>Determine, for one or more members, data points associated with the respective member<br>Determine, for one or more members and one or more data points associated with the member and a number of providers associated with the respective member and a particular data point |
| Network based detection | Services not rendered<br>Phantom provider | Identify entities<br>Identify non-flagged providers who are strongly connected to previously flagged providers using, for example, a weighted data structure (e.g., a weighted provider-provider bidirectional graph in which edges are weighted by members shared between providers)<br>Identify providers who have a certain proportion of members who are associated with flagged providers or non-flagged providers strongly connected to previously flagged providers using, for example, an unweighted data structure (e.g., an unweighted provider-member graph)<br>Identify unflagged providers who have a certain proportion of members who have a minimum weight using, for example, a data structure (e.g., a provider-member graph where member nodes are valued as number of edges to flagged providers or non-flagged providers strong connected to previously flagged providers)<br>Referral networks can also be considered as a factor |
| Associative rule mining | Unbundling | Identify entities<br>Perform periodic item set detection for sets of procedure codes associated with a common period of time and/or patient. Additionally and/or alternatively, perform associative rule mining and select for statistically significant rules to describe each provider lead<br>Look for statistically significant sets of procedure codes (e.g., certain sets of procedure codes that are billed at high frequency by a certain provider but not by other providers)<br>Prioritize providers based on number of such outlier item sets. Additionally and/or alternatively, prioritize providers based on exposure over proposed upcoding scheme |
| Procedure groupings | Upcoding | Apply a statistical test on coding categories data sets (e.g., a Wilcoxon signed rank test) |

3.6 Other Functional Disclosure

In some cases, two or more providers may be assigned the same broad specialty code, but perform different procedures. This may cause the results of one or more of the fraud detection models to be less accurate than desired. Thus, the server 102 (or any other system or device described herein) may use a clustering technique to reassign providers to different subspecialty codes based on the types of procedures (as identified by the procedure code or procedure code groups associated with the providers) performed by the providers.

Fraud detection embodiments described herein facilitate, without limitation, one or more of the following:

- Leverage knowledge and findings of different investigative teams, which reduces repeated work among the different teams.
- Rank leads associated with total exposure fraud higher over, for example, statistical confidence
- Early detection of fraud: Because fraud is temporally transient, fraud that is detected in advance of claim payout (e.g., detection of unpaid leads) is factored into ranking the list of identified leads.
- Fraud is adaptive: Models are correspondingly adaptive.
- Analysts gravitate toward what they know and their area of specialty: Explanatory information presentation with each of the identified leads aids in relating new leads to previously analyzed leads and/or familiar schemes.
- High precision: Investigative process is slow and laborious. Thus, false positive leads are more inefficient use of resources than false negative leads. Surfacing false positive leads over false negative leads also facilitates early adoption or acceptance of new/improved model use, and in establishing and maintaining trust in the system 100.
- Model transparency and/or tunability may be preferred over model accuracy
- Positive labels are limited and not representative of space of fraud: At least some of the leads not identified as fraud are fraudulent leads that are unknown or presently undetectable.
- Negative labels are rare or non-existent: Analysts tend to not label identified leads clearly determined to be not fraud. System 100 facilitates capture of this type of information.
- Determination of fraud may not be a binary determination.
- Data relationships may be many-to-many as opposed to one-to-many
- Incorporates analysts' domain knowledge and discovery of new fraud schemes.
- Support labeling processes: Insufficient labeling results in repeated work and limited ability to learn from previous investigations. More comprehensive labeling enhances precision and recall of schemes. Enable labeling of weak fraud signals, which may add up to a strong signal of fraud.
- Learning from past examples
- Facilitate discovery and exploration of new fraud schemes by analysts.
- Facilitate various annotation, recordkeeping, and collaboration capabilities on analysts' workspaces.
- Facilitate dashboard of savings due to fraud detection, fraud detection accuracy statistics, etc.

4.0 Example User Interface with Explanatory Information

FIG. 5 illustrates a user interface 500 illustrating an example lead summary report for a particular identified lead. As illustrated in FIG. 5, the particular identified lead may be a lead identified using the outlier detection #2 fraud detection model. The user interface 500 includes a header section 502, a plurality of widget panels or sections 510, 512, 514, and 522, and a plurality of tabs 516, 518, and 520. The header section 502 may include an analyst assignment element 504, a fraud detection model or scheme element 506, and/or a lead name element 508. The element 506 can identify the particular fraud detection model(s) or scheme(s) upon which the particular identified lead was deemed to be potentially fraudulent. As an example, element 506 may specify that the particular identified lead was found from the "providing unnecessary procedures" scheme. The analyst assignment element 504 can specify whether the summary report (and correspondingly the initial assessment of the particular identified lead) is assigned to a particular analyst or is unassigned. As depicted, the summary report is shown as unassigned. Alternatively, the summary report may be assigned to a particular analyst that has, for example, known expertise or is a specialist in assessing providing unnecessary procedures scheme frauds. The element 508 can include the name of the provider corresponding to the particular identified lead.

Widget panel 510 may include biographical or basic provider information. In some embodiments, the widget panel 510 may be included in most or all lead summary reports. The widget panel 512 may include notes, comments, and/or explanatory information about the associated fraud scheme(s) (and/or free form information that the person or system that generated the particular identified lead deemed to be relevant). As described above, for a lead identified using the outlier detection #2 fraud detection model, the explanatory information may include template text and specific values associated with the identified lead object that are auto-populated into the template text that describe the meaning of a mutual information score (without actually providing the mutual information score, which may be meaningless to a fraud analyst). As illustrated in the widget panel 512, the template text may be the non-underlined text and the specific values auto-populated into the template text may be underlined. The underlining is for illustrative purposes and may or may not be present in an actual lead summary report. Thus, instead of providing the mutual information score, the fraud analyst may be provided with information that more clearly identifies why potential fraud was detected.

In some embodiments, the summary report includes a user feedback widget or the content of the user feedback widget may be included in the widget panel 512. As an example, content of the user feedback widget may comprise, without limitation, a set of user feedback choices from which the user selects once review of the particular identified lead has been completed: "This lead is great, I recommend pursuing," "I had to do further digging but this lead is interesting enough to continue pursuing," "This lead is awful, don't provide more like these in the future," "I need more information to make a decision on this lead," or "Other." Providing a set number of textual feedback choices rather than a set of scores (e.g., 1, 2, 3, 4, or 5 stars) or free form feedback options preemptively addresses potential scoring bias or manual review of user feedback for use in lead summary report design.

The widget panel 514 may comprise an example of codes indicated by the provider, unique claims associated with each code, the amount billed by the provider for each code, and the amount received by the provider for each code.

The widget panel 522 is displayed under tab 518 and includes a map with a location of the provider indicated in the map (e.g., based on the address of the provider). Additional widget panels under tabs 516 and 520 (not shown) may include paid to TIN data for the provider and/or a breakdown or distribution of procedure codes for the provider. Alternatively, the widget panel 522 or the additional widget panels may be displayed without tabs, may be displayed in additional page(s) of the summary report, and/or the like.

Although not shown, the summary report may include additional user interactive features. For example, the summary report may include a "freeze" button or other indicator for the fraud analyst to create documentation based on the summary report.

Each widget depicted in the user interface 500 may be independent of the other widgets in the summary report. Each of the widgets can display the same or different type of lead data or content from the other widgets, can display the lead data in the same or different format from the other widgets (e.g., tables, bar graph, line graph, text, map, input field, etc.), or otherwise be configured specific to the type of lead data that facilitates fraud or non-fraud determination or other assessment to be made by the fraud analyst.

5.0 Data Architecture

The techniques described herein may be practiced with respect to medical claims data stored using a variety of different data structures and/or formats, depending on the embodiment. Example searchable data structures for storing medical claims data and other ancillary data records are described below. However, the examples given below are for illustrative purposes only, and the techniques described herein are not limited to any particular structures or formats.

In an embodiment, health care event objects are maintained in a health care event repository comprising one or more databases that store the health care event objects, provider objects are maintained in a provider repository comprising one or more databases that store the provider objects, patient objects are maintained in a patient repository comprising one or more databases that store the patient objects, and pharmacy objects are maintained a pharmacy repository comprising one or more databases that store the pharmacy objects. Other repositories may exist for other types of data objects. The one or more databases that constitute a repository may overlap between some or all of the repositories. Or, the repositories may be maintained separately.

In an embodiment, each of the objects described above, and other objects described herein, are generated from import operation(s) of data from various sources, such as an insurer's databases, a provider's health care records, pharmacy records, government records, and other public records. The import operation may be repeated periodically or on occasions to update the objects and/or add new objects. The import operation may involve various ETL operations that normalize the source data to fit data models such as described herein.

In an embodiment, some or all of the objects described herein are not necessarily stored in any permanent repository, but are rather generated from the source data "on demand" for the purpose of the various analyses described herein.

5.1 Logical Object Types

In an embodiment, a data object is a logical data structure that comprising values for various defined fields. A data object may be stored in a variety of underlying structure(s), such as a file, portions of one or more files, one or more XML elements, a database table row, a group of related database table row(s), and so forth. An application will read the underlying structure(s), and interpret the underlying structure(s) as the data object. The data object is then processed using various steps and algorithms such as described herein.

In one embodiment, the modeled object types conceptually include, without limitation: claim objects, such as medical physician claims, medical outpatient claims, medical inpatient claims, and pharmacy claims; patient objects; provider/prescriber objects; prescription objects; pharmacy objects; and fraud objects. Many variations on these combinations of objects are possible.

5.2 Sources

In an embodiment, some or all of the health care data objects are generated from source data hosted by a variety of sources. Example sources include provider or insurer sources such as: a claims processing database; a policy administration database, a provider network database, a membership/eligibility database, a claim account database, a pharmacy benefit database, a lab utilization gateway database, pharmacy claims database, an authentication call list, a tip-off hotline database, and a billing/accounts receivable database. Example sources further include government or public data repositories such as public health records, repositories of USPS zip codes, National Drug Codes, Logical Observation Identifiers Names and Codes, and/or National Provider Identifiers, an OIG exclusion list, and a List of Excluded Individuals/Entities. Of course, many other sources of data are also possible.

5.3 Databases

In an embodiment, data from the various data sources are passed through an ETL layer to form a set of databases. For example, the databases may include: Product, Organization, Geography, Customer, Member, Provider, Claim Statistics, Claim Aggregation, Claim Financial, Pharmacy Claims, Lab Results, and Revenue. The databases may store the various data objects described herein. The data objects may instead be arranged in a variety of other configurations.

5.4 Example Ontology

In an embodiment, ontology for preventing health care fraud comprises the some or all of the following data object types: Claim objects, Drug objects, Member objects, Pharmacy objects, Plan Benefit objects, Prescriber objects, and Provider objects.

Each claim object represents a health care claim, which is a request for reimbursement from an insurer for health care expenses. There may be multiple types of claim objects, including claims objects for prescriptions, claim objects for laboratory tests, claim objects for medical procedures, and claim objects for other types of services. In an embodiment, a claim object comprises, among other elements, values for one or more the following types of attributes: unique system identifier(s), associated member identifier, allowed amount, claim status (paid, rejected, or reversed), date submitted, covered Medicare Plan D amount, date of service, estimated number of days prescription will last, paid dispensing fee, prescribed drug identifier, ingredient cost paid, mail order identifier, non covered plan paid amount, number of authorized refills, other payer amount, member plan type, amount paid by patient, deductible amount, pharmacy system identifier, prescriber system identifier, prescription written date, quantity dispensed, prescription claim number, service fee (the contractually agreed upon fee for services rendered), total amount billed by processor. Different fields may be specific to different types of providers or claims.

Each drug object represents a specific drug. In an embodiment, a drug object comprises, among other elements, values for one or more of the following types of attributes: unique system identifier(s), American Hospital Formulary Service Therapeutic Class Code, generic status indicator (brand name or generic), drug name trademark status (trademarked, branded generic, or generic), dosage form, DEA class code, generic class name, over-the-counter indicator, drug strength, generic code number, generic code sequence, generic product index, maintenance drug code, product identifier qualifier, product service identifier, unit of measure, National Drug Code, and so forth.

Each member object represents a specific member of a health care plan. There may be multiple collections of members for different insurers and/or types of plans, and each collection may have a different structure. In an embodiment, a member object comprises, among other elements, values for one or more the following types of attributes: one or more unique system identifiers, maximum service month, the number of months enrolled in each particular year covered by the data, first name, last name, gender, date of birth, address, city, state, zip code, county, telephone, social security number, additional address and other contact fields for different types of contact information (e.g., work, temporary, emergency, etc.), a plan benefit system identifier, an enrollment source system, and so forth.

In an embodiment, a member object may further include or be associated with tracking data that log changes to values for the above attributes over time. For example, a separate Member Detail object may exist, values for the above attributes for each month or year the member was covered by a plan. Each Member Detail object may include a month and/or year attribute and a member identifier to tie it back to its associated Member object.

Each pharmacy object represents a specific pharmacy. In an embodiment, a pharmacy object comprises, among other elements, values for one or more the following types of attributes: unique system identifier(s), pharmacy dispenser class (independent, chain, clinic, or franchise, government, alternate), pharmacy dispenser type (community/retail, long term, mail order, home infusion therapy, non-pharmacy, Indian health service, Department of Veterans Affairs, institutional, managed care, medical equipment supplier, clinic, specialty, nuclear, military/coast guard, compounding), affiliate code, service provider identifier, service provider identifier qualifier, and so forth.

Each plan benefit object represents a specific plan benefit. In an embodiment, a plan benefit object comprises, among other elements, values for one or more the following types of attributes: unique system identifier(s), contract number, provider identifier, start date, end date, package key, and so forth.

Each prescriber object represents a specific prescriber of drugs. In an embodiment, a plan benefit object comprises, among other elements, values for one or more the following types of attributes: unique system identifier(s), first name, last name, prescriber identifier(s), prescriber identifier qualifier(s) (e.g., not specified, NPI, Medicaid, UPIN, NCPDP ID, State License Number, Federal Tac ID, DEA, or State Issued), specialty code, and so forth. Prescriber objects and provider objects may in some cases represent or be associated with a same real world entity, but prescriber objects reflect data from a different source than provider objects. In some embodiments attributes from prescriber objects and provider objects may be combined into a single object. In other embodiments, the two objects are logically separate, but can be correlated together if they do in fact represent the same entity.

Each provider object represents a specific provider of health care services. In an embodiment, a provider object comprises, among other elements, values for one or more the following types of attributes: medical provider identification number (both text and numeric), provider type (medical professional, healthcare organization), provider status (active contract or no activate contract), various contract line indicators, one or more process exception hold effective dates, one or more process exception type codes, a date that the medical provider identification number was created, a date the provider record became inactive, an organization type code to indicate provided services or specialties, a Medicare identifier, provider medical degree, provider primary specialty, last name, first name, middle initial, name suffix, middle name, gender, social security number, federal tax identifier, date of birth, graduation date, medical school, credential status code, credential description, current credential cycle, current credential type (initial, re-credential, hospital-based, delegated, alliance, discontinued, empire initial, excluded from process, terminated), credential indicator, credential organization identifier, credential organization accreditation date, credential organization indicator, universal provider identifier, bill type (HCFA, UB92, UB04, composite), provider information source, provider claims classifier, email, last update type, address, and so forth.

Additional data objects that may be in a health care ontology are set forth in the attached appendix.

5.5 Metrics

Various example metrics for automatically identifying, prioritizing, and/or investigating leads are described below. In an embodiment, metrics may be utilized in formulating certain searches, such that claim records may be located based on how various claim attributes compare to various metrics. In an embodiment, metrics may be directly searchable. In an embodiment, metrics may be calculated and displayed in various visualization interfaces associated with search results. For instance, metrics may be calculated for a set of search results, and/or data from a search result may be compared to metrics for a group of records at large. Metrics may be calculated and stored periodically, or calculated on demand.

Metrics related to member objects may include, without limitation, one or more of: an average and/or standard deviation of Schedule 2 prescriptions per month; a count of drug abuse diagnoses; a count, average, and/or standard deviation of ER visits per year; a count of distinct providers that have written prescriptions for the member; a count of distinct pharmacies that have filled prescriptions for the member; a sum amount paid by an insurer on behalf of the member; an average and/or standard deviation amount paid per month; a sum number of pills dispensed per month; an average days between prescriptions; an average and/or standard deviation prescriptions per month for the member; an average and/or standard deviation for member medical claims per month; a count of total Schedule 2 prescriptions; a count of total Schedule 3 prescriptions; a count of total prescriptions; an average and/or standard deviation for net amount paid per diagnosis category; a count of durable medical equipment claims; a count of methadone overdoses; a count of opiate poisoning; a methadone dependence indicator; and/or a sum DME Net Amount paid.

Metrics related to provider objects may include, without limitation, one or more of: an average and/or sum total billed by provider; a sum net amount paid to the provider; an average and/or standard deviation net amount paid per month; a standard deviation for net amount paid per month by specialty; a standard deviation for net amount paid per month by specialty by geography, an average prescription pill quantity; an average prescription number of refills; a count of prescription claims not paid; a count of prescription claims; a count of medical claims; an average and/or standard deviation for prescription claims per patient; an average and/or standard deviation for medical claims per patient; a percentage of Schedule 2 drugs; a percentage of Schedule 3 drugs; a percentage of Schedule 2 drugs by specialty; a percentage of Schedule 3 drugs by specialty; a count of distinct patients of the provider; a count of distinct pharmacies to which patients of the provider are sent; a standard deviation of distinct diagnoses made by the provider by specialty; a count of distinct procedures performed by the provider; a count of clinic ownerships; a standard deviation for net amount paid to the provider by diagnosis; a count of durable medical equipment prescriptions made; a percentage of in-network claims attributed to the provider; and/or an estimated total days in business.

Metrics related to provider objects may further include, without limitation, one or more of: average claims per day; average net amount paid per claim; average net amount paid per month; average patient count; average pharmacy count; distinct count of diagnoses; a histogram of diagnoses; distinct count of procedures; and/or a histogram of procedures.

Metrics related to pharmacy objects may include, without limitation, one or more of: average net amount paid by the insurer; maximum and/or average net amount paid per prescriber; count of claims; percentage of filled prescriptions that involved a Schedule 2 category of drugs; percentage of filled prescriptions that involved a Schedule 3 category of drugs; average and/or sum dispensing fee; days in business, percentage of filled prescriptions that involved a brand name drug; a count of distinct drug names in the prescriptions; percentage of filled prescriptions that involved a high reimbursement drug; percentage of filled prescriptions that involved a drug of potential abuse; a percentage of claims for refills; average and/or standard deviation distance traveled by customers to the pharmacy; a count of co-located pharmacies; percentage of filled prescriptions that involved small refills; percentage of claims that were reversed; a count of claims not paid; average billed per patient; average billed per prescriber; average claims per patient; average claims per prescriber.

Metrics related to diagnosis objects may include, without limitation, one or more of: a histogram of CPT-4, ICD-9, ICD-10 or HCPCS procedures; a histogram of co-occurring diagnoses; average net amount paid per year per patient; average total net amount paid per patient; a histogram of drug names prescribed; an indicator of drug abuse; and/or an indicator of drug-seeking behavior.

Metrics related to procedure objects may include, without limitation, one or more of: a histogram of diagnoses; a histogram of co-occurring procedures on the same date per patient; and a total, average, minimum, and/or maximum procedure count per patient per diagnosis.

Metrics related to drug objects may include, without limitation, one or more of: maximum drug quantity per patient per year; and/or minimum, maximum, and/or average net amount paid.

Metrics related to prescription claim objects may include, without limitation, one or more of: distance traveled to pharmacy; distance traveled to prescriber; an indicator of whether the prescription is for a drug of abuse; a standard deviation of net amount paid; an indicator of whether the prescribed patient's gender is appropriate to the prescription; an indicator of whether the prescription claim is for an expensive branded drug; and/or an indicator of whether the prescription claim is for a Schedule 2 commonly abused drug.

Metrics related to medical claim objects may include, without limitation, one or more of: distance traveled to physician; an indicator of whether the claim is indicative of drug abuse; and/or a standard deviation of net amount paid per procedure.

In an embodiment, various triggers may be generated based on the above metrics. The triggers are monitored functions of one or more of the metrics. When a monitored function has a value that is within a particular range, the trigger identifies one or more lead objects that are associated with the one or more metrics.

For example, in an embodiment, triggers may include members visiting three of more independent pharmacies in a day, members obtaining prescriptions in three of more states within a month, or members receiving multiple and subsequent home rental medical equipment. Each of these triggers would produce a member lead object. Another example trigger is multiple new patient office visits for the same patient in a three year period. This trigger would produce a member lead object.

An additional example of a trigger is a Top Pharmacies by Drugs Commonly Abused trigger. For each month, this trigger lists the pharmacy that has dispensed the most amount of one of the commonly abused drugs. An additional example of a trigger is a Top Patients Receiving Drugs Commonly Abused trigger. For each month, this trigger lists the patient receiving the most amount of one of the commonly abused drugs. An additional example of a trigger is a Top Prescribers of Drugs Commonly Abused trigger. This trigger lists the providers who have prescribed the most amount of one of the most commonly abused drugs. An additional example of a trigger is a Mailbox Matching trigger. For each region of interest (as denoted by a City and State), this trigger lists providers who have a practice address that matches the location of a UPS drop box. An additional example of a trigger is a Frequent NPIs trigger. For each region of interest (as denoted by a City and State), this trigger lists provider locations receiving multiple NPIs in a short time frame.

6.0 Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 6:
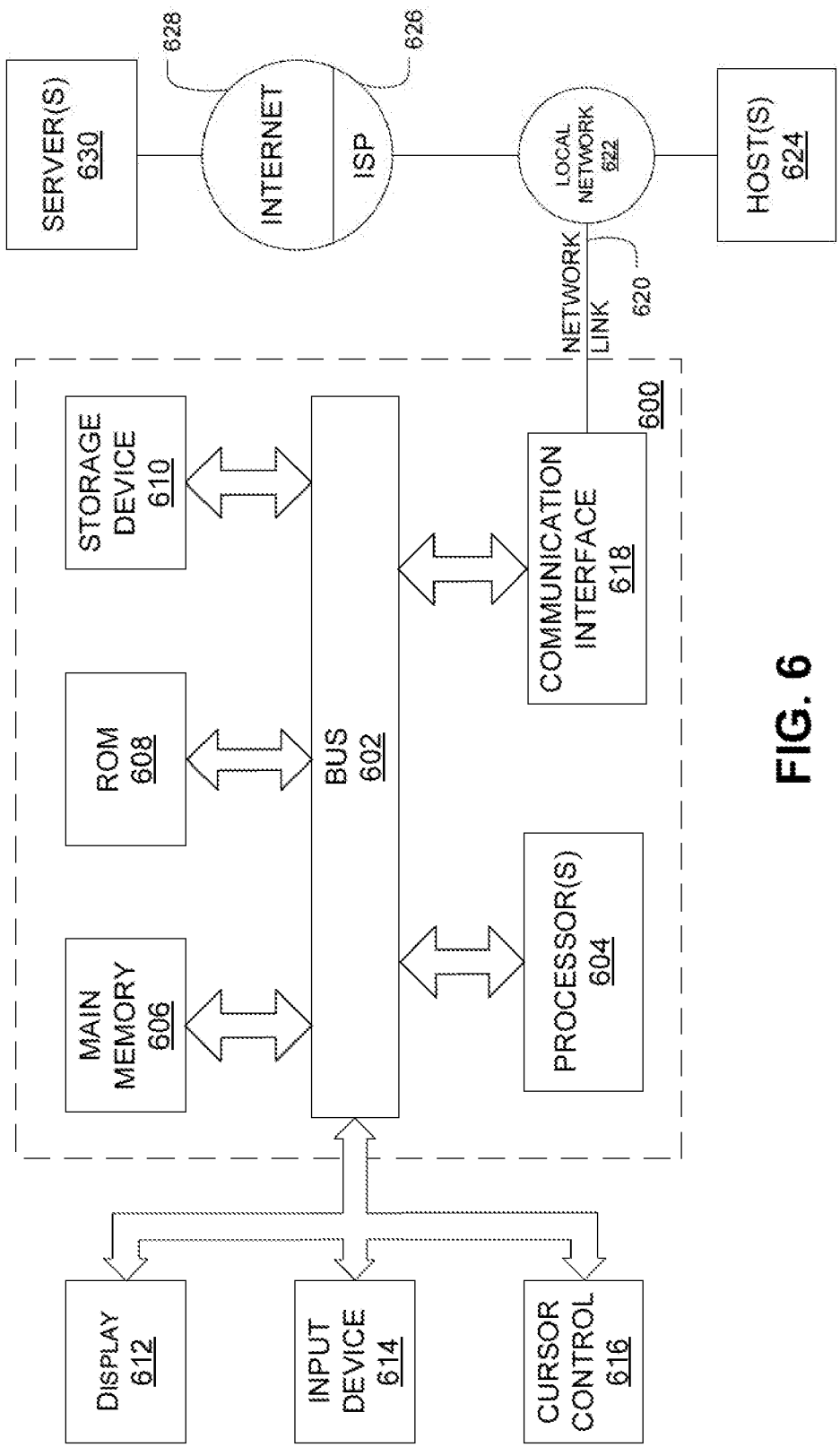
FIG. 6 illustrates a block diagram of an example computer system upon which embodiments of the present disclosure may be implemented.

For example, FIG. 6 is a block diagram that illustrates a computer system 600 upon which embodiments of the present disclosure may be implemented. Computer system 600 includes a bus 602 or other communication mechanism for communicating information, and a hardware processor 604 coupled with bus 602 for processing information. Hardware processor 604 may be, for example, a general purpose microprocessor.

Computer system 600 also includes a main memory 606, such as a random access memory (RAM) or other dynamic storage device, coupled to bus 602 for storing information and instructions to be executed by processor 604. Main memory 606 also may be used for storing temporary variables or other intermediate information during execution of instructions to be executed by processor 604. Such instructions, when stored in non-transitory storage media accessible to processor 604, render computer system 600 into a special-purpose machine that is customized to perform the operations specified in the instructions.

Computer system 600 further includes a read only memory (ROM) 608 or other static storage device coupled to bus 602 for storing static information and instructions for processor 604. A storage device 610, such as a magnetic disk or optical disk, is provided and coupled to bus 602 for storing information and instructions.

Computer system 600 may be coupled via bus 602 to a display 612, such as a cathode ray tube (CRT) or liquid crystal display (LCD), for displaying information to a computer user. An input device 614, including alphanumeric and other keys, is coupled to bus 602 for communicating information and command selections to processor 604. Another type of user input device is cursor control 616, such as a mouse, a trackball, or cursor direction keys for communicating direction information and command selections to processor 604 and for controlling cursor movement on display 612. This input device typically has two degrees of freedom in two axes, a first axis (e.g., x) and a second axis (e.g., y), that allows the device to specify positions in a plane.

Computer system 600 may implement the techniques described herein using customized hard-wired logic, one or more ASICs or FPGAs, firmware and/or program logic which in combination with the computer system causes or programs computer system 600 to be a special-purpose machine. According to one embodiment, the techniques herein are performed by computer system 600 in response to processor 604 executing one or more sequences of one or more instructions contained in main memory 606. Such instructions may be read into main memory 606 from another storage medium, such as storage device 610. Execution of the sequences of instructions contained in main memory 606 causes processor 604 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device 610. Volatile media includes dynamic memory, such as main memory 606. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 602. Transmission media can also take the form of acoustic or light waves, such as those generated during radio-wave and infra-red data communications.

Various forms of media may be involved in carrying one or more sequences of one or more instructions to processor 604 for execution. For example, the instructions may initially be carried on a magnetic disk or solid state drive of a remote computer. The remote computer can load the instructions into its dynamic memory and send the instructions over a telephone line using a modem. A modem local to computer system 600 can receive the data on the telephone line and use an infra-red transmitter to convert the data to an infra-red signal. An infra-red detector can receive the data carried in the infra-red signal and appropriate circuitry can place the data on bus 602. Bus 602 carries the data to main memory 606, from which processor 604 retrieves and executes the instructions. The instructions received by main memory 606 may optionally be stored on storage device 610 either before or after execution by processor 604.

Computer system 600 also includes a communication interface 618 coupled to bus 602. Communication interface 618 provides a two-way data communication coupling to a network link 620 that is connected to a local network 622. For example, communication interface 618 may be an integrated services digital network (ISDN) card, cable modem, satellite modem, or a modem to provide a data communication connection to a corresponding type of telephone line. As another example, communication interface 618 may be a local area network (LAN) card to provide a data communication connection to a compatible LAN. Wireless links may also be implemented. In any such implementation, communication interface 618 sends and receives electrical, electromagnetic or optical signals that carry digital data streams representing various types of information.

Network link 620 typically provides data communication through one or more networks to other data devices. For example, network link 620 may provide a connection through local network 622 to a host computer 624 or to data equipment operated by an Internet Service Provider (ISP) 626. ISP 626 in turn provides data communication services through the world wide packet data communication network now commonly referred to as the "Internet" 1028. Local network 622 and Internet 628 both use electrical, electromagnetic or optical signals that carry digital data streams. The signals through the various networks and the signals on network link 620 and through communication interface 618, which carry the digital data to and from computer system 600, are example forms of transmission media.

Computer system 600 can send messages and receive data, including program code, through the network(s), network link 620 and communication interface 618. In the Internet example, a server 630 might transmit a requested code for an application program through Internet 628, ISP 626, local network 622 and communication interface 618.

The received code may be executed by processor 604 as it is received, and/or stored in storage device 610, or other non-volatile storage for later execution.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

7.0 Terminology

Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof

What is claimed is:

1. A method for processing a large amount of dynamically updating data, the method comprising:
    training, by one or more hardware processors, a fraud detection model using machine learning techniques and one or more sets of training data, wherein the fraud detection model comprises a plurality of metrics, wherein the one or more sets of training data comprises one or more known instances of misuse, and wherein the one or more sets of training data comprise training data that, when used to train the fraud detection model, increases a rate of convergence in machine learning and improves accuracy of the fraud detection model;
    automatically detecting, by the one or more hardware processors, an instance of suspected misuse by an entity associated with a claim using the fraud detection model and first data transformed into a format that conforms with the fraud detection model;
    in response to automatically detecting an instance of suspected misuse by the entity associated with the claim, calculating, by the one or more hardware processors, a degree of similarity between the detected instance and each of the one or more known instances of misuse, each of the one or more known instances of misuse corresponding to a known entity associated with one or more respective claims;
    automatically identifying, by the one or more hardware processors, one or more similar known instances of misuse from among the one or more known instances of misuse based on the degree of similarity calculated between the detected instance of suspected misuse and each of the one or more known instances of misuse;
    generating, for the detected instance of suspected misuse and by the one or more hardware processors, explanatory information that comprises text in a natural language format that corresponds with the detected instance of suspected misuse, the explanatory information including an indication of similarity of the detected instance of suspected misuse to the identified one or more similar known instances of misuse;
    causing, by the one or more hardware processors, the explanatory information to be auto-populated between sets of template text in a first user interface element and presented with information about the detected instance of suspected misuse in a user interface, wherein the first user interface element further depicts selectable user feedback choices associated with the detected instance of suspected misuse;

receiving, by the one or more hardware processors, feedback data associated with the detected instance of suspected misuse based on a selection of one or more of the selectable user feedback choices, wherein the feedback data comprises an indication that the detected instance of suspected misuse is an instance of actual misuse and an explanation of why the detected instance of suspected misuse is an instance of actual misuse generated in response to input from a user;

transforming, by the one or more hardware processors, the feedback data into a first metric, separate from the plurality of metrics, that quantifies a characteristic of the instance of actual misuse; and updating, by the one or more hardware processors, the fraud detection model using the first metric to form an improved fraud detection model that detects a second instance of suspected misuse that was not detected by the fraud detection model.

2. The method of claim 1, wherein calculating the degree of similarity comprises calculating a weighted distance between the detected instance and each of the one or more known instances of misuse.

3. The method of claim 1, wherein calculating the degree of similarity comprises calculating the degree of similarity using a k-nearest neighbor (KNN) technique.

4. The method of claim 1, further comprising:
prior to automatically detecting the instance, automatically detecting the one or more known instances of misuse as being suspected of misuse using the fraud detection model;
receiving, from an independent source, a confirmation of misuse of the one or more known instances of misuse;
wherein the one or more known instances of misuse are available for calculating the degree of similarity after receiving the confirmation.

5. The method of claim 4, further comprising receiving, from the independent source, the confirmation of misuse for the detected instance, wherein the detected instance becomes a known instance of misuse for a next one of a detected instance.

6. The method of claim 4, wherein the independent source comprises one or more claim misuse analysts.

7. The method of claim 1, wherein the fraud detection model is an outlier detection model, and wherein automatically detecting an instance of suspected misuse by an entity associated with a claim further comprises:
determining, for the entity, types of procedures performed by the entity;
determining, for each type of procedure, a first percentage of members that receive services from the entity that receive the respective type of procedure;
analyzing, for each type of procedure performed by the entity, the first percentage and second percentages of members that receive the respective type of procedure determined for other entities to determine a threshold value; and
determining that the first percentage is less than the threshold value.

8. The method of claim 1, wherein the entity is one of a health care provider, a health care member, a patient, or a pharmacy.

9. One or more non-transitory machine-readable media storing instructions which, when executed by one or more hardware processors, cause:

training a fraud detection model using machine learning techniques and one or more sets of training data, wherein the fraud detection model comprises a plurality of metrics, and wherein the one or more sets of training data comprises one or more known instances of misuse;

automatically detecting an instance of suspected misuse by an entity associated with a claim using the fraud detection model and first data transformed into a format that conforms with the fraud detection model;

in response to automatically detecting an instance of suspected misuse by the entity associated with the claim, calculating a degree of similarity between the detected instance and each of the one or more known instances of misuse, each of the one or more known instances of misuse corresponding to a known entity associated with one or more respective claims;

automatically identifying one or more similar known instances of misuse from among the one or more known instances of misuse based on the degree of similarity calculated between the detected instance of suspected misuse and each of the one or more known instances of misuse;

generating, for the detected instance of suspected misuse, explanatory information that comprises text in a natural language format that corresponds with the detected instance of suspected misuse, the explanatory information including an indication of similarity of the detected instance of suspected misuse to the identified one or more similar known instances of misuse;

causing the explanatory information to be auto-populated between sets of template text in a first user interface element and presented with information about the detected instance of suspected misuse in a user interface, wherein the first user interface element further depicts selectable user feedback choices associated with the detected instance of suspected misuse;

receiving feedback data associated with the detected instance of suspected misuse based on a selection of one or more of the selectable user feedback choices, wherein the feedback data comprises an indication that the detected instance of suspected misuse is an instance of actual misuse and an explanation of why the detected instance of suspected misuse is an instance of actual misuse generated in response to input from a user;

transforming the feedback data into a first metric, separate from the plurality of metrics, that quantifies a characteristic of the instance of actual misuse; and updating the fraud detection model using the first metric to form an improved fraud detection model that detects a second instance of suspected misuse that was not detected by the fraud detection model.

10. The one or more non-transitory machine-readable media of claim 9, wherein calculating the degree of similarity comprises calculating the degree of similarity using a k-nearest neighbor (KNN) technique.

11. The one or more non-transitory machine-readable media of claim 9, wherein the instructions, when executed by the one or more hardware processors, further cause:
prior to automatically detecting the instance, automatically detecting the one or more known instances of misuse as being suspected of misuse using the fraud detection model;
receiving, from an independent source, a confirmation of misuse of the one or more known instances of misuse;
wherein the one or more known instances of misuse are available for calculating the degree of similarity after receiving the confirmation.

12. The one or more non-transitory machine-readable media of claim 9, wherein the entity comprises a health care provider, a health care member, a patient, or a pharmacy.

13. A computer system configured to process a large amount of dynamically updating data, the computer system comprising:
- one or more databases including a plurality of claims data;
- a detection component, at least partially implemented by computing hardware, configured to:
  - train a fraud detection model using machine learning techniques and one or more sets of training data, wherein the fraud detection model comprises a plurality of metrics, and wherein the one or more sets of training data comprises one or more known instances of misuse,
  - automatically detect an instance of suspected misuse by an entity associated with a claims data from among the plurality of claims data using the fraud detection model and first data transformed into a format that conforms with the fraud detection model;
- a similarity component, at least partially implemented by computing hardware, configured to identify one or more known instances of misuse similar to the detected instance, each of the one or more known instances of misuse corresponding to a known entity associated with a respective claims data from among the plurality of claims data;
- a generation component, at least partially implemented by computing hardware, configured to generate, for the detected instance, misuse explaining information that comprises text in a natural language format that corresponds with the detected instance, the misuse explaining information including an indication of similarity of the detected instance to each of the one or more known instances of misuse identified by the similarity component, and causing the misuse explaining information to be auto-populated between sets of template text in a first user interface element for presentment in a user interface, wherein the first user interface element further depicts selectable user feedback choices associated with the detected instance; and
- a model refinement component, at least partially implemented by computing hardware, configured to:
  - receive feedback data associated with the detected instance of suspected misuse based on a selection of one or more of the selectable user feedback choices, wherein the feedback data comprises an indication that the detected instance of suspected misuse is an instance of actual misuse and an explanation of why the detected instance of suspected misuse is an instance of actual misuse generated in response to input from a user,
  - transform the feedback data into a first metric, separate from the plurality of metrics, that quantifies a characteristic of the instance of actual misuse, and
  - update the fraud detection model using the first metric to form an improved fraud detection model that detects a second instance of suspected misuse that was not detected by the fraud detection model.

14. The computer system of claim 13, wherein the similarity component identifies the one or more known instances of misuse similar to the detected instance based on calculation of a weighted distance between the detected instance and each of the one or more known instances of misuse.

15. The computer system of claim 13, wherein the fraud detection model is a function of a combination of weighted features of at least one misuse.

16. The computer system of claim 15, wherein the detection component automatically detects, prior to automatic detection of the instance, the one or more known instances of misuse as being suspected of misuse using the fraud detection model, and further comprising a user interface component, at least partially implemented by computing hardware, configured to receive from an independent source, a confirmation of misuse of the one or more known instances of misuse,
  - wherein the one or more known instances of misuse are available for identification by the similarity component after the user interface component receives the confirmation.

17. The computer system of claim 15, further comprising a user interface component, at least partially implemented by computing hardware, configured to receive from an independent source, a confirmation of misuse for the detected instance, wherein the detected instance becomes a known instance of misuse for a next one of a detected instance.

* * * * *